(12) United States Patent
Delcamp et al.

(10) Patent No.: US 12,409,238 B2
(45) Date of Patent: Sep. 9, 2025

(54) SILICONE-BASED DYES WITH SHORT WAVELENGTH INFRARED ABSORPTION AND EMISSION AND METHODS FOR MAKING AND USING THE SAME

(71) Applicant: UNIVERSITY OF MISSISSIPPI, Oxford, MS (US)

(72) Inventors: Jared Heath Delcamp, Oxford, MS (US); David Ndaleh Dodah Nghombui, Oxford, MS (US); William Edward Meador, Oxford, MS (US)

( * ) Notice: Subject to any disclaimer, the term of this patent is extended or adjusted under 35 U.S.C. 154(b) by 0 days.

(21) Appl. No.: 17/662,574

(22) Filed: May 9, 2022

(65) Prior Publication Data
US 2022/0370641 A1   Nov. 24, 2022

Related U.S. Application Data

(60) Provisional application No. 63/269,337, filed on Mar. 14, 2022, provisional application No. 63/268,508, filed on Feb. 25, 2022, provisional application No. 63/186,472, filed on May 10, 2021.

(51) Int. Cl.
| | |
|---|---|
| *A61K 49/00* | (2006.01) |
| *C09B 57/00* | (2006.01) |
| *C09K 11/06* | (2006.01) |

(52) U.S. Cl.
CPC .......... *A61K 49/0021* (2013.01); *C09B 57/00* (2013.01); *C09K 11/06* (2013.01); *C09K 2211/1007* (2013.01); *C09K 2211/1018* (2013.01)

(58) Field of Classification Search
CPC ................ A61K 49/0021; C09K 11/06; C09K 2211/1007; C09K 2211/1018; C09B 57/00
See application file for complete search history.

(56) References Cited

U.S. PATENT DOCUMENTS

| | | |
|---|---|---|
| 6,350,431 B1 | 2/2002 | Snow et al. |
| 2003/0157021 A1 | 8/2003 | Klaveness et al. |
| 2009/0263658 A1* | 10/2009 | Alberius ............. C09B 67/0013 428/402.2 |
| 2016/0296639 A1 | 10/2016 | Hanaoka et al. |
| 2019/0262366 A1 | 8/2019 | Aneja et al. |

OTHER PUBLICATIONS

ISR Int'l Appln. No. pct/us22/72214 mailed Sep. 22, 2022.
(Koide, Yet al.) Design strategy for germanium-rhodamine based pH-activatable near-infrared fluorescence probes suitable for biological applications. Communications Chemistry, vol. 2, Article No. 94, Aug. 9, 2019, hllps://doi.org/10.1038/s42004-019-0194-4, pp. 1-8.
(Rathnamalala, CSL et al.) Donor-Acceptor-Donor NIR 11 Emissive Rhodindolizine Dye Synthe-sized by C—H Bond Functionalization. Journal of Organic Chemistry, vol. 84, No. 20, 2019, Sep. 3, 2019, doi: 10.1021/acs.ioc.9b01860, pp. 13186-13193.
(Rajapaksha, I el al.) New Design Strategy Toward NIR I Xanthene Based Dyes. Journal of Organic Chemistry, vol. 85, Aug. 24, 2020, pp. 12108-12116; p. 12109.
Search Report for European Application 2280509.8 mailed Feb. 26, 2025.
Takuya Myochin et al: "Development of a Series of Near-Infrared Dark Quenchers Based on Si-rhodamines and Their Application to Fluorescent Probes", Journal of the American Chemical Society, vol. 137, No. 14, Apr. 15, 2015 (Apr. 15, 2015), pp. 4759-4765, XP05524 7 486, ISSN: 0002-7863, DOI: 10.1021 /jacs.5b00246.

* cited by examiner

*Primary Examiner* — Michael G. Hartley
*Assistant Examiner* — Leah H Schlientz
(74) *Attorney, Agent, or Firm* — Thomas | Horstemeyer, LLP

(57) ABSTRACT

Described herein are new silicone-based compounds that have short wavelength infrared (SWIR) absorption and emission. The silicone-based compounds are readily accessible and obtainable on large scale with high purity through simple purification procedures. In one aspect, the silicone-based compounds have an absorption extending into the SWIR region and an emission maximum in the SWIR region which is promising for biological imaging applications.

6 Claims, 12 Drawing Sheets ative or by using an indolizine heterocycle on the xanthene core to extend the π-conjugated system onto the donor group beyond the atom attached to the xanthene core.

SILICONE-BASED DYES WITH SHORT WAVELENGTH INFRARED ABSORPTION AND EMISSION AND METHODS FOR MAKING AND USING THE SAME

CROSS-REFERENCE TO RELATED APPLICATIONS

This application claims the benefit of and priority to co-pending U.S. Provisional Patent Application Nos. 63/186,472, filed on May 10, 2021; 63/268,508, filed on Feb. 25, 2022; and 63/269,337, filed on Mar. 14, 2022. The contents of each provisional application are incorporated by reference herein in their entireties.

STATEMENT REGARDING FEDERALLY SPONSORED RESEARCH OR DEVELOPMENT

This invention was made with government support under grant number 1757220, awarded by the National Science Foundation. The government has certain rights in the invention.

BACKGROUND

Fluorescence biological imaging in the short wavelength infrared (SWIR or NIR-II) spectra region from 1000 nm to 1700 nm is a powerful technique for high definition real-time non-invasive monitoring of biological systems.[1-9] Importantly, small molecule fluorescent probes have made a deep impact in chemical biology, clinical diagnosis and drug discovery.[10-13] However, few probes exist in the SWIR region where background noise due to tissue autofluorescence and biological matrix absorption are minimal which allows for the deepest tissue penetration.[3, 14] The lack of SWIR probes limits fluorescence imaging application progress in terms of imaging depth and with regard to multiplex imaging. Many of the reported probes in the SWIR region are based on carbon nanotubes or quantum dots which eventually suffer from indefinite distribution in organs like the liver and spleen[15, 16] and also from slow excretion kinetics.[17-19] Small molecule based organic dyes for NIR-II imaging are rarely documented with cyanines being the most commonly reported class of small molecule materials in the SWIR region.[20-23]

Xanthene based dyes are popular fluorophore probes in the visible region due to their excellent molecular brightness (MB where MB=ε×φ and ε is the molar absorptivity and φ is the quantum yield) and biocompatibility.[24] The majority of the materials utilizing xanthene cores rely on amine (rosamines) or oxygen/nitrogen (rosol) mixed donor groups to delocalize the positive charge throughout the π-system. These systems typically fall short of the SWIR spectral region for absorption and emit primarily at higher energy than the SWIR region.[25-27] The use of an indolizine heterocycle on the xanthene core allows for extension of the π-conjugated system onto the donor group beyond the atom attached to the xanthene core allowing SWIR emission.

SUMMARY

Described herein are new silicone-based compounds that have short wavelength infrared (SWIR) absorption and emission. The silicone-based compounds are readily accessible and obtainable on large scale with high purity through simple purification procedures. In one aspect, the silicone-based compounds have an absorption extending into the SWIR region and an emission maximum in the SWIR region which is promising for biological imaging applications.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

the absorption and emission spectrum of $^{Tol}$SiRosindz in anhydrous THF solution.

Figure 3:
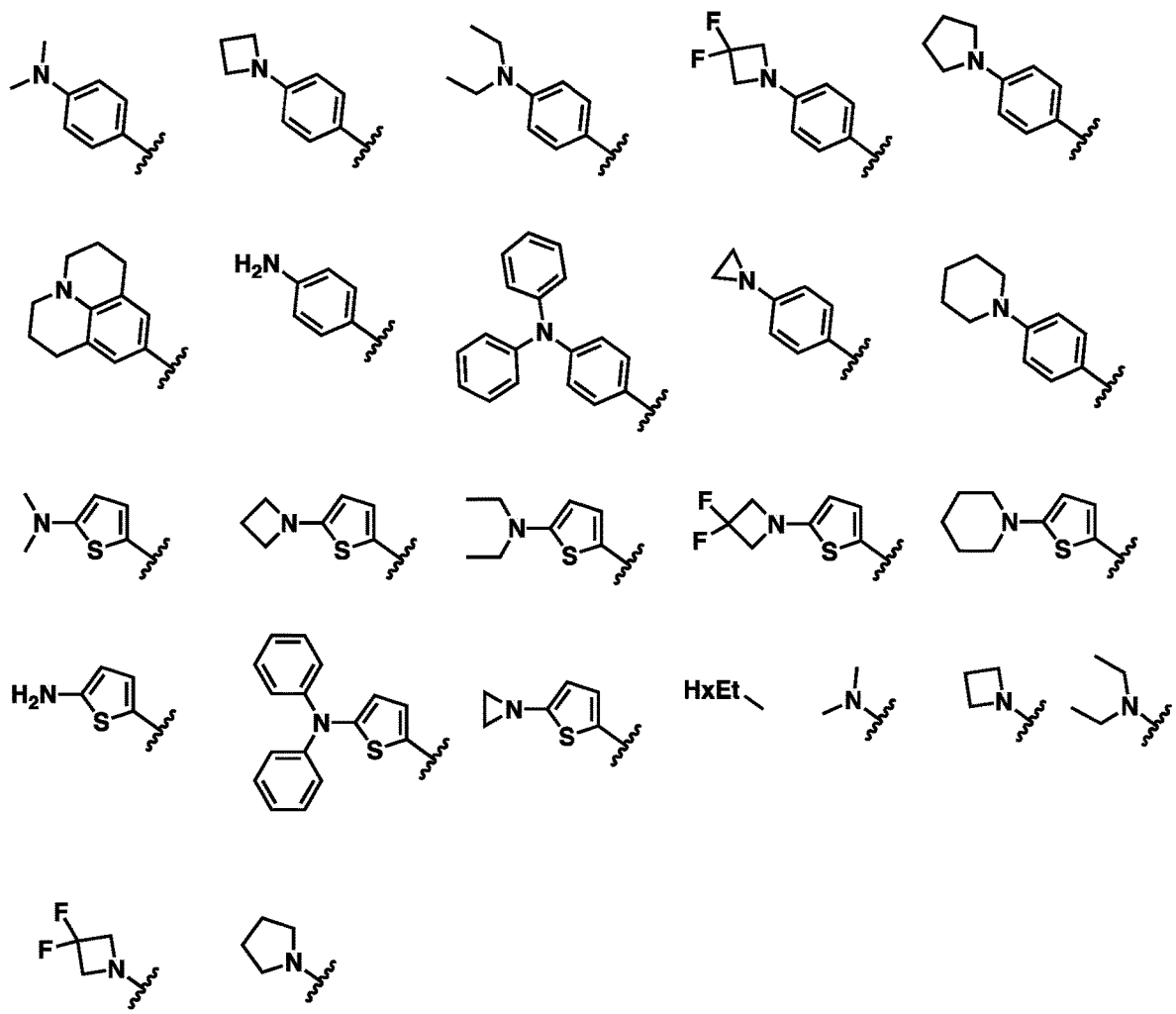
FIG. 3 shows examples of different groups that can be present in the silicone-based compounds described herein.

FIG. 3 shows the absorption spectrum of RhodlndzPyNMe$_2$ in DCM solution.

Figure 4:
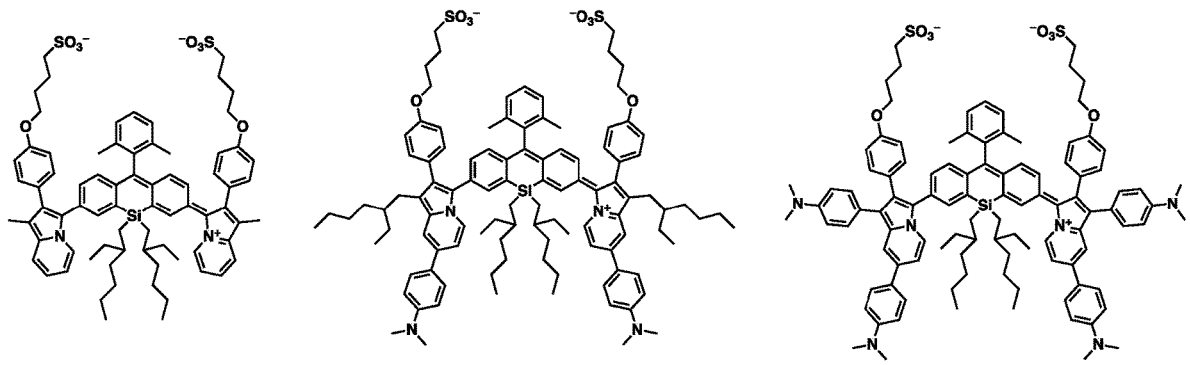
FIG. 4 shows of silicone-based compounds described herein with anionic groups.

FIG. 4 shows the absorption spectrum of RhodlndzAmd in DCM.

Figure 5:
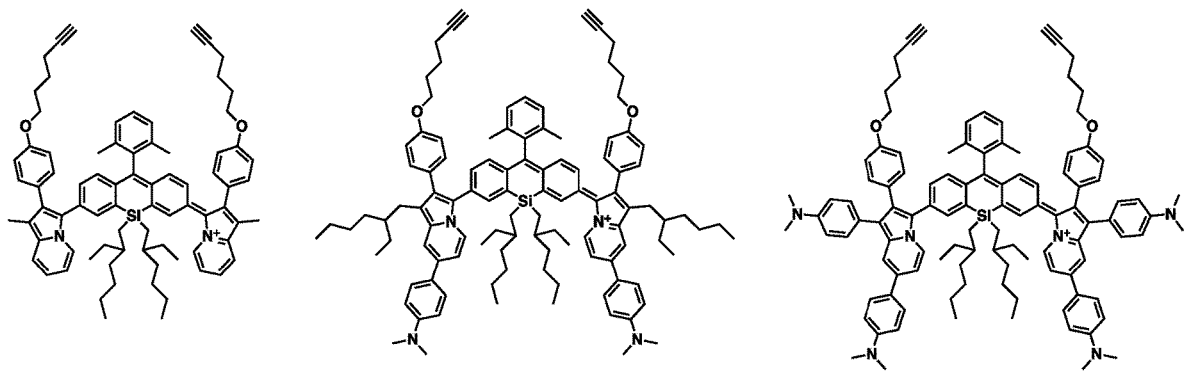
FIG. 5 shows of silicone-based compounds described herein with alkyne groups.

FIG. 5 shows exemplary indolizine compounds described herein.

Figure 6:
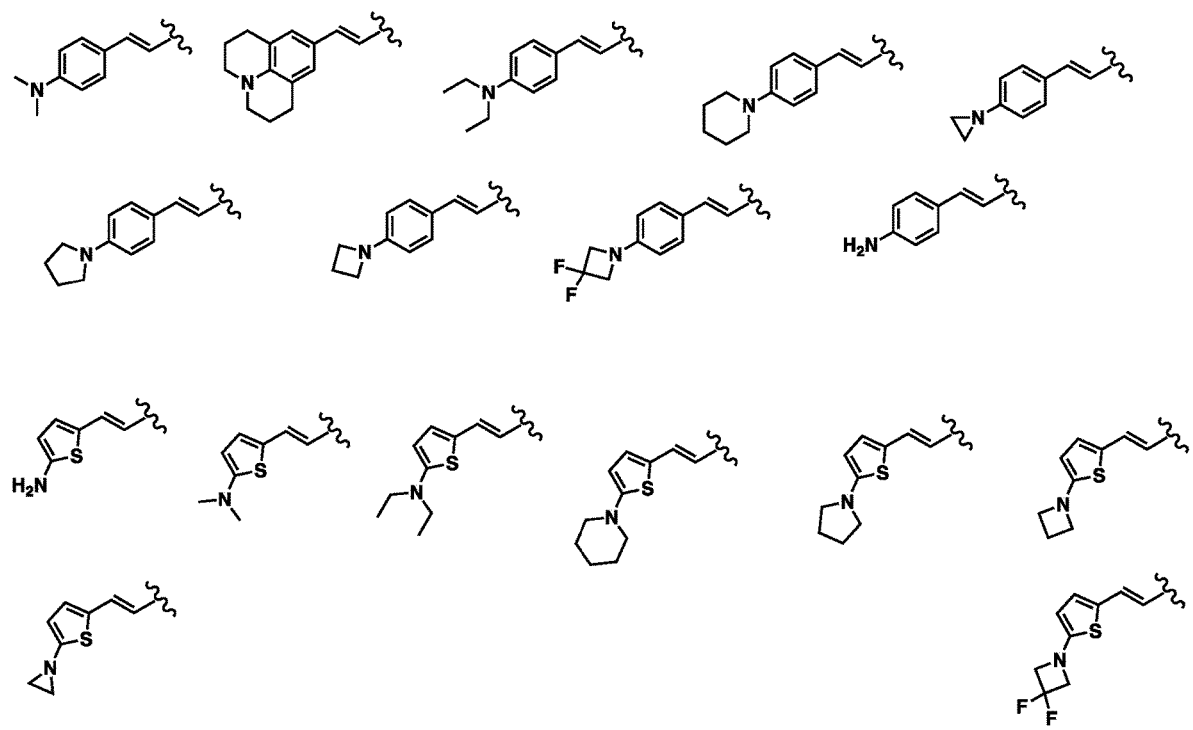
Figure 7:
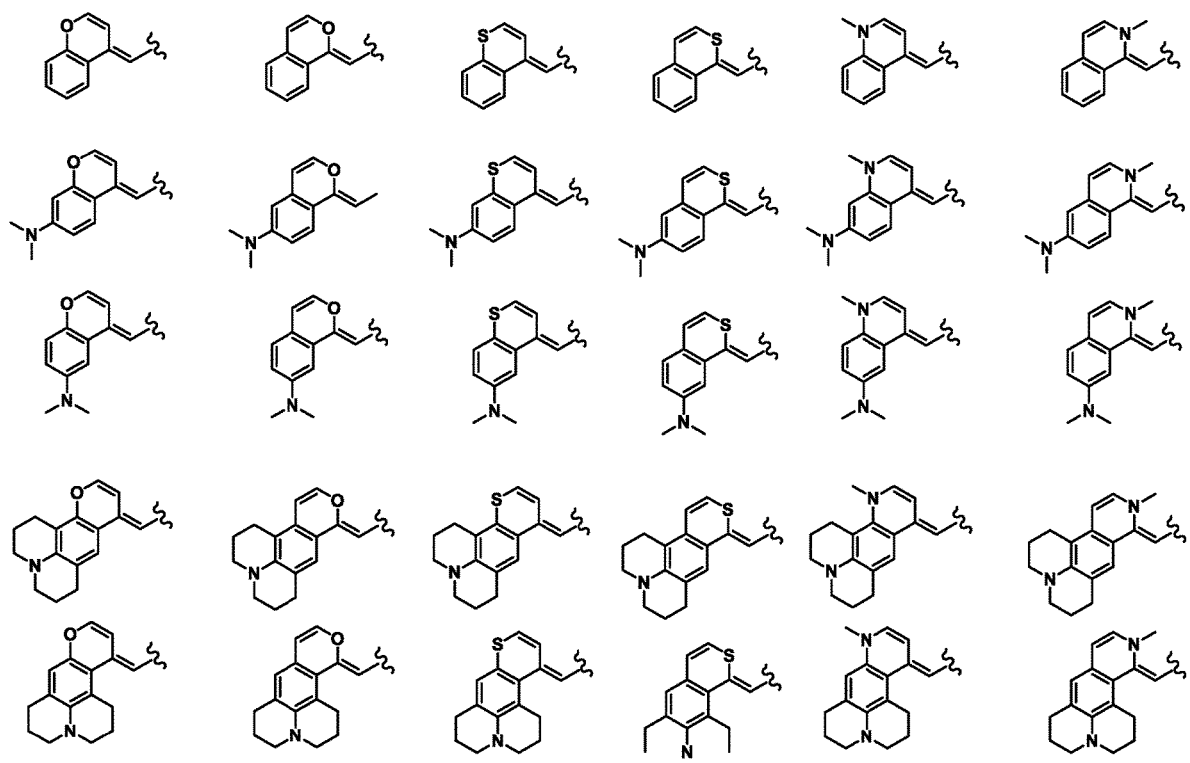
Figure 8:
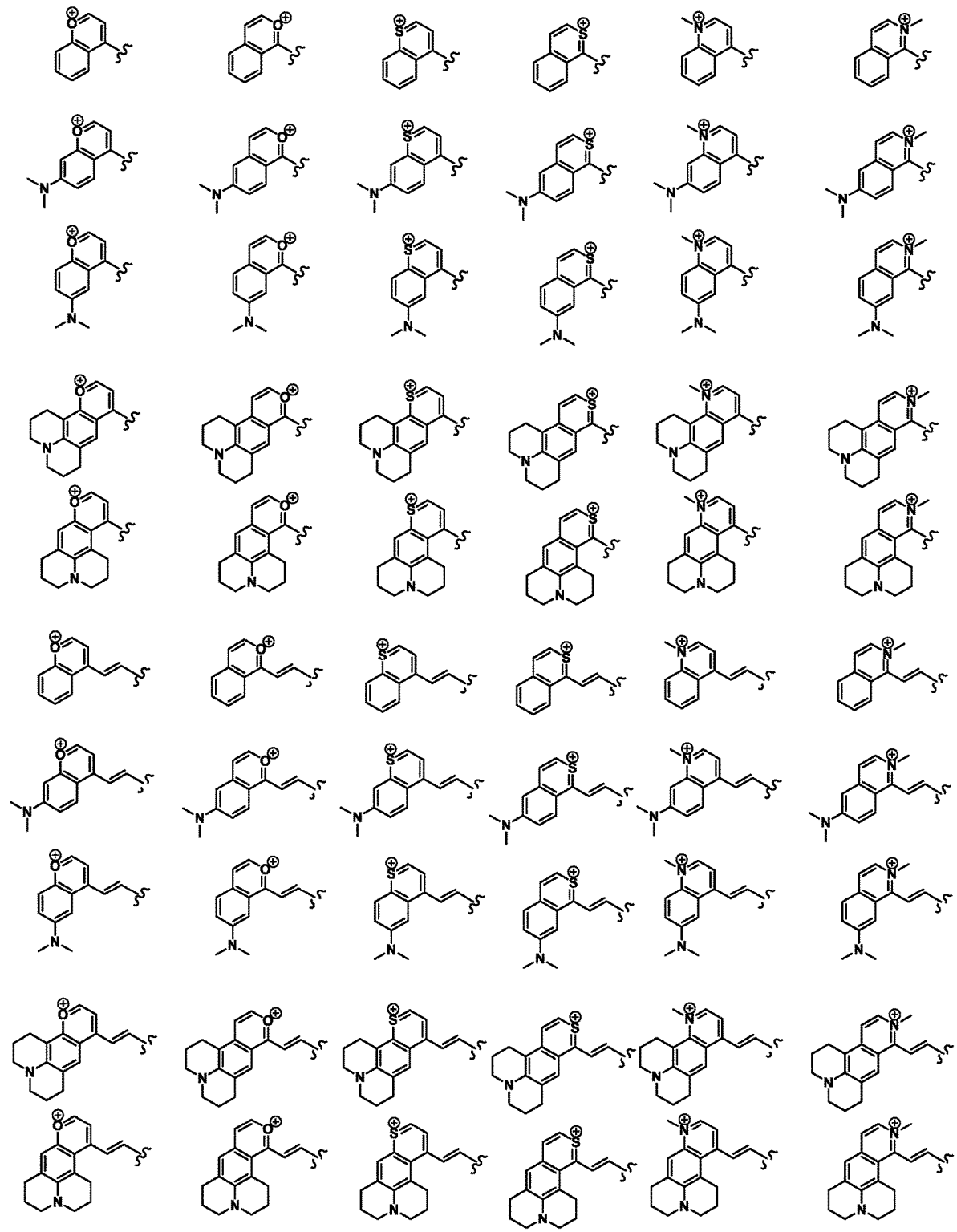

FIGS. 6-8 shows examples of different aromatic and polycyclic groups that can be present in the silicone-based compounds described herein.

Figure 9:
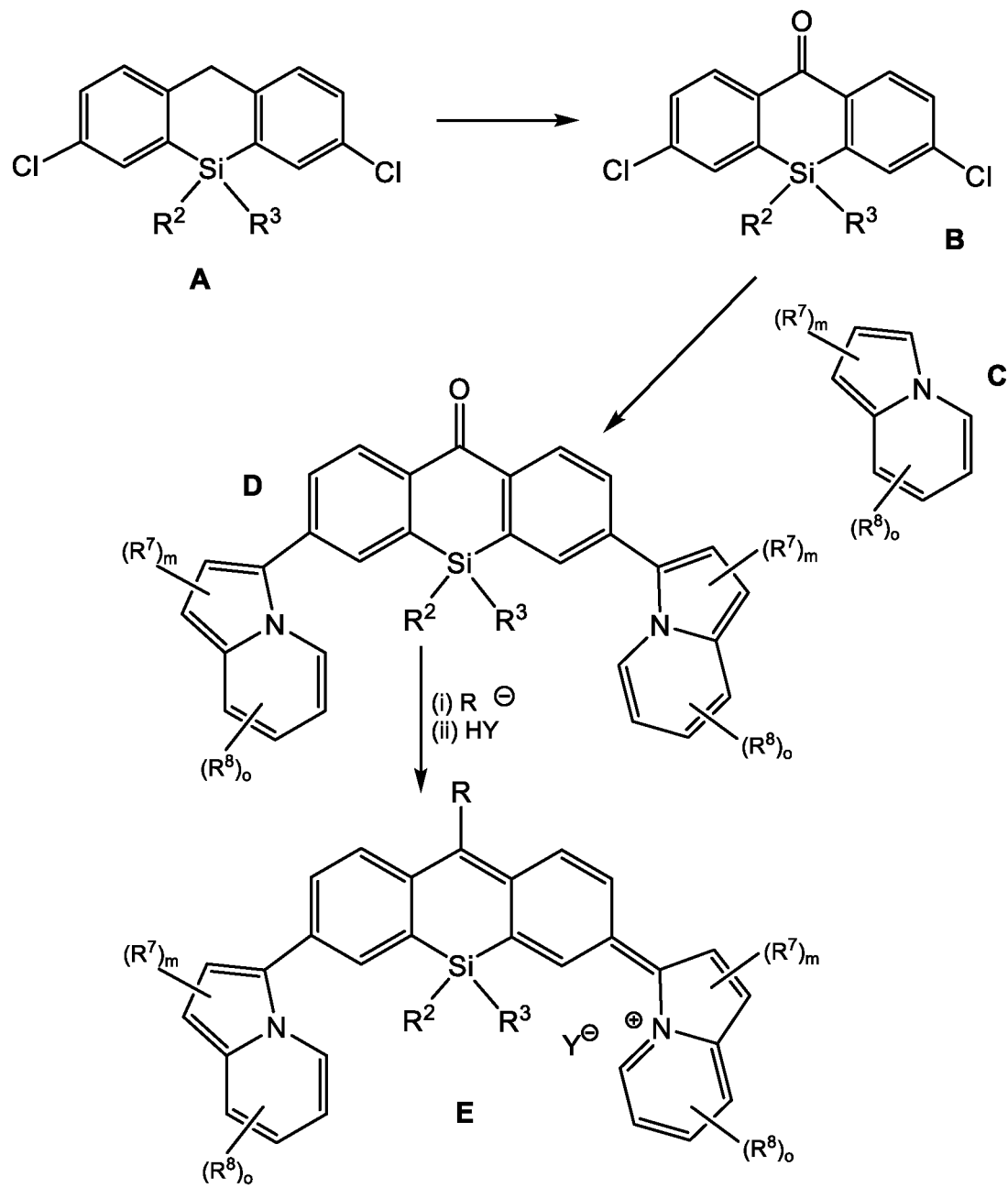

FIG. 9 provides a general synthetic scheme for synthesizing the silicone-based compounds described herein.

Figure 10:
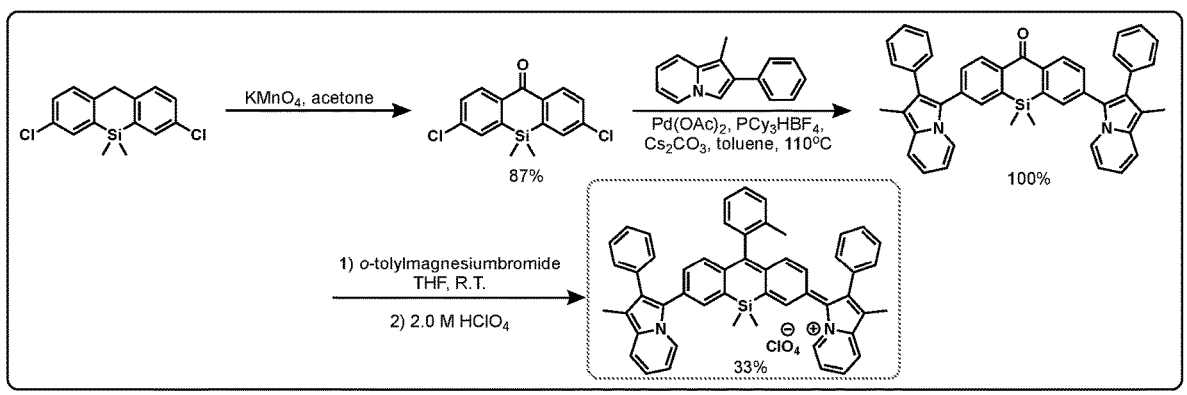

FIG. 10 provides a synthetic scheme for synthesizing a silicone-based compound described herein.

Figure 11:
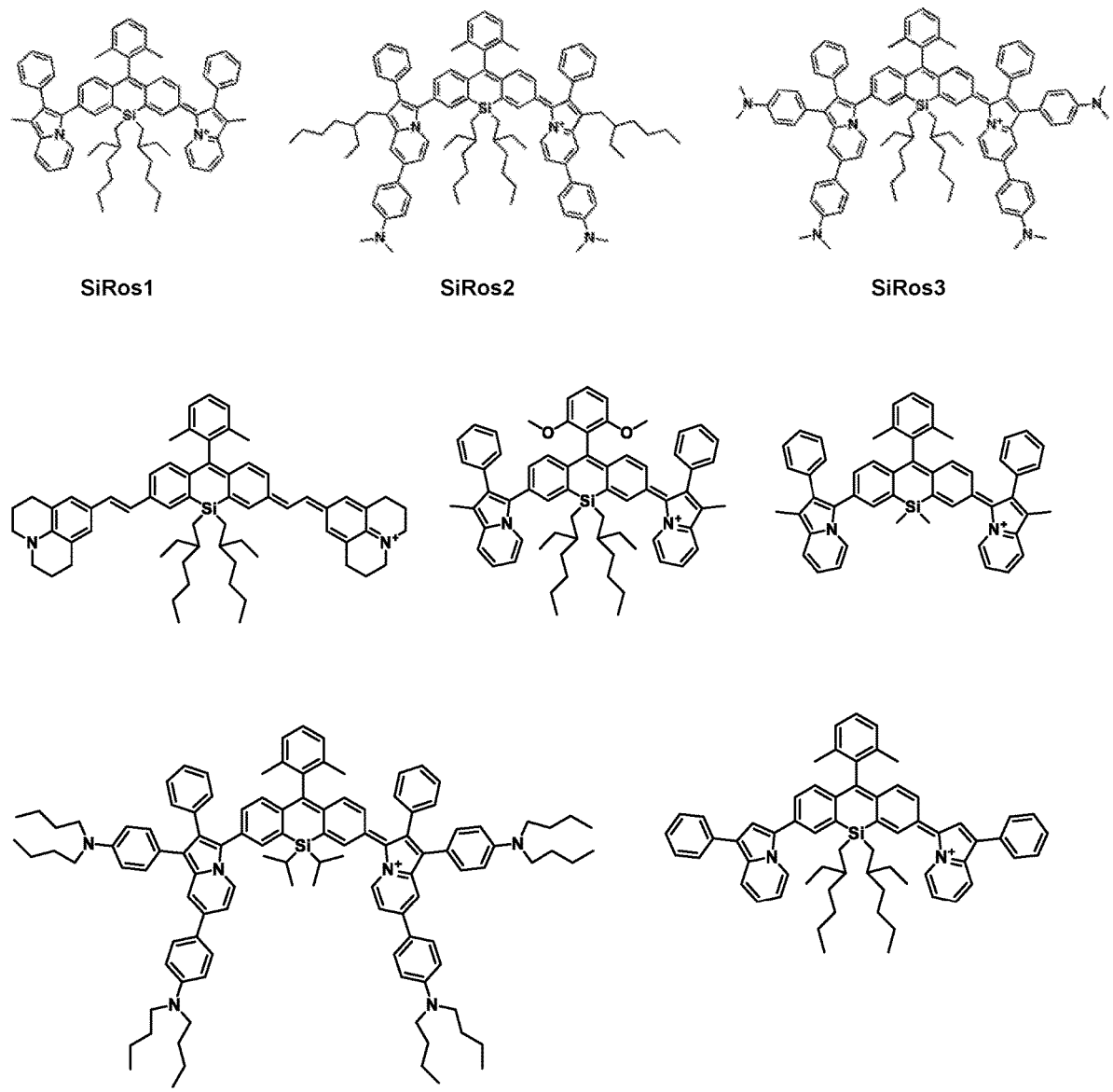

FIG. 11 provides the structures of exemplary silicone-based compounds described herein.

Figure 12:
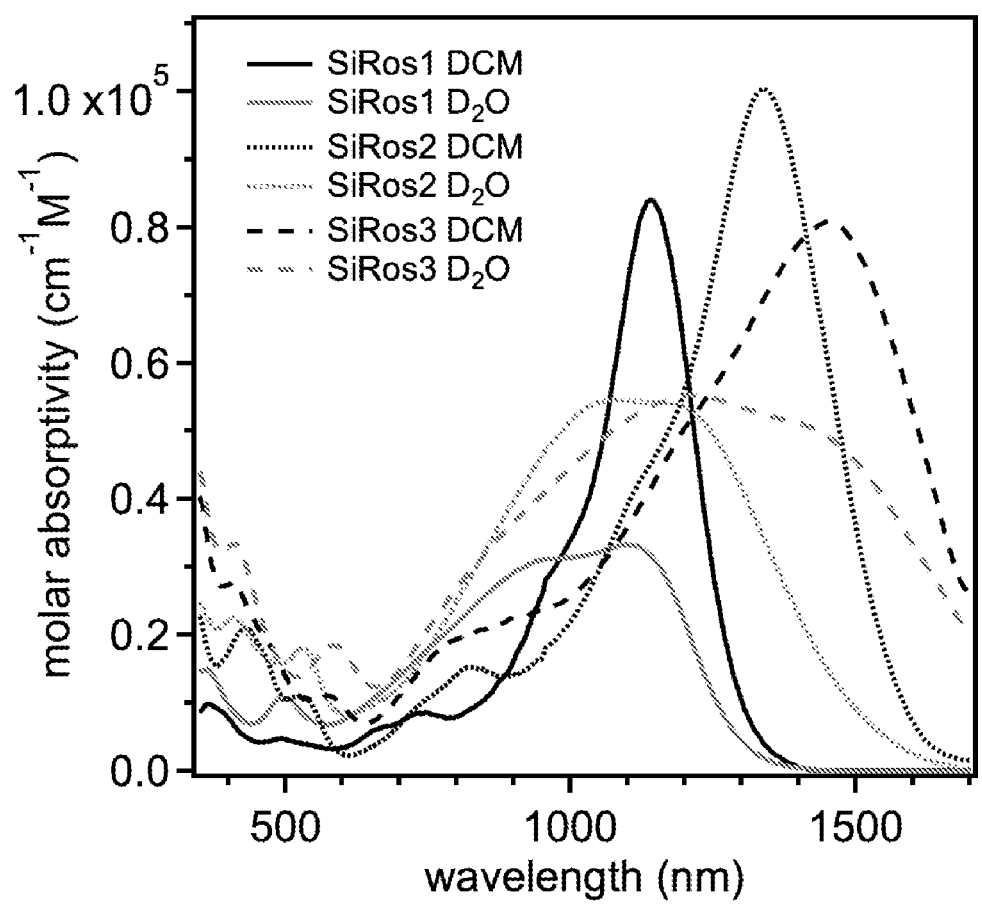

FIG. 12 shows the absorption curve data for SiRos1, SiRos2, and SiRos3.

Figure 13:
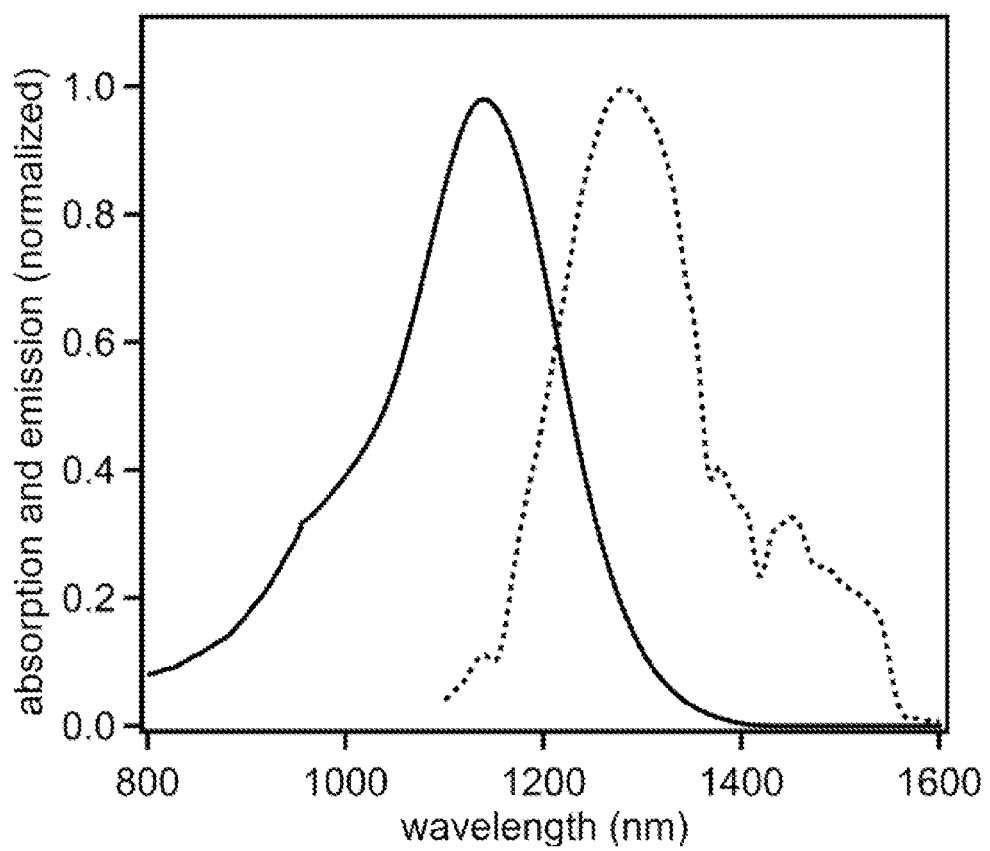

FIG. 13 shows the absorption (full line) and emission (dashed line) curves for SiRos1 in DCM.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a solvent" includes, but is not limited to, mixtures or combinations of two or more such solvents, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "alkyl group" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl group" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "aryl group" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, amide, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl. Fused aryl groups including, but not limited to, indene and naphthalene groups are also contemplated.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$—OA$^2$ or —OA$^1$—(OA$^2$)$_a$-OA$^3$, where "a" is an integer of from 1 to 200 and A$^1$, A$^2$, and A$^3$ are alkyl and/or cycloalkyl groups The term "alkenyl" as used herein is a hydrocarbon group of from 2 to 24 carbon atoms with a structural formula containing at least one carbon-carbon double bond. Asymmetric structures such as (A$^1$A$^2$)C═C(A$^3$A$^4$) are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The terms "halo," "halogen" or "halide," as used herein can be used interchangeably and refer to F, Cl, Br, or I.

The term "carboxylic acid group" as used herein is represented by the formula —C(O)OH.

The term "ester group" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein.

The term "amide group" as used herein is represented by the formula —OC(O)N$A^2A^3$ or —C(O)N$A^2A^3$, where $A^2$ and $A^3$ can be independently hydrogen, alkyl, cycloalkyl, alkenyl, cycloalkenyl, alkynyl, cycloalkynyl, aryl, or heteroaryl group as described herein.

The term "amino group" as used herein is represented by the formula —N$A^2A^3$, where $A^2$ and $A^3$ can be independently hydrogen, alkyl, cycloalkyl, alkenyl, cycloalkenyl, alkynyl, cycloalkynyl, aryl, or heteroaryl group as described herein.

The term "carboxylate group" as used herein is represented by the formula —C(O)$O^\ominus$.

The term "sulfate group" as used herein is represented by the formula —OS(O)$_2O^\ominus$.

The term "sulfonate group" as used herein is represented by the formula —S(O)$_2O^\ominus$.

The term "phosphate group" as used herein is represented by the formula —OP(O)$O_2^{-2}$.

The term "phosphonate group" as used herein is represented by the formula —P(O)$O_2^2$.

As used herein, the term "effective amount" refers to an amount that is sufficient to achieve the desired modification of a physical property of the composition or material. For example, an "effective amount" of a silicone-based compound refers to an amount that is sufficient to produce the desired amount of fluorescence in a subject that can be subsequently detected. The specific level in terms of wt % in a composition required as an effective amount will depend upon a variety of factors including the amount and type of silicone-based compound, type of cell or tissue, and co-administration of additional therapies.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to conduct the methods of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

Silicone-Based Compounds

Described herein are new silicone-based compounds that that have short wavelength infrared (SWIR) absorption and emission. In one aspect, the silicone-based compound has the structure I

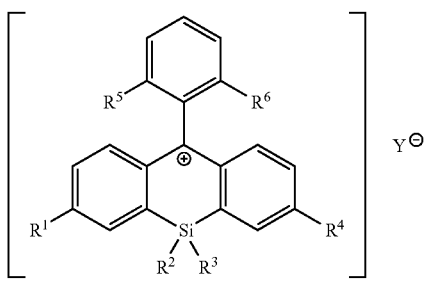

wherein

R¹ and R⁴ are independently a heteroaryl group bonded to the phenyl ring via a carbon atom of the heteroaryl group;

R² and R³ are each an alky group or an aryl group;

R⁵ and R⁶ are independently hydrogen, an alkyl group, or an alkoxy group, wherein R⁵ and R⁶ are not both hydrogen; and Y is a counterion.

The silicone-based compounds described herein possess a positive charge that is delocalized throughout the ring structure. Although the positive charge is identified at a specific carbon atom in structure I, the positive charge can be delocalized throughout the fused phenyl rings as well as the phenyl covalently bonded to the carbon where the positive charge is indicated in structure I. Additionally, depending upon the nature of R⁴, the positive charge can be delocalized in the R⁴ groups as well. Provided below are some exemplary structures showing the delocalization of the positive charge present in structure I.

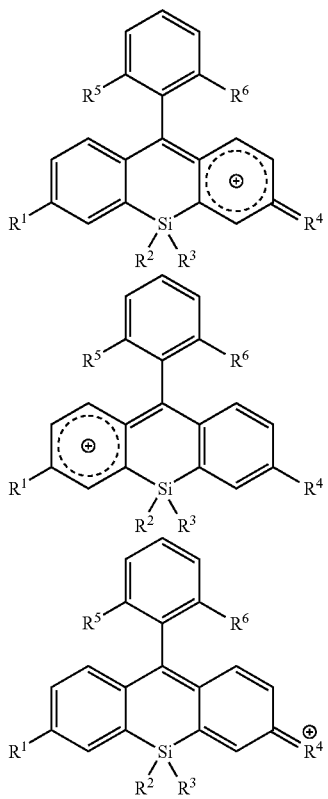

In one aspect, the silicone-based compounds described herein can be symmetrical compounds. Referring to structure I, when R¹=R⁴, R²=R³, and R⁵=R⁶, the molecule is symmetrical. In other aspects, the silicone-based compounds described herein can be asymmetrical compounds, where R¹≠R₄, R²≠R³, and/or R⁵≠R⁶.

In one aspect, R² and R³ in structure I are each a $C_1$ to $C_{10}$ alkyl group. In another aspect, R² and R³ in structure I are the same $C_1$ to $C_{10}$ alkyl group. In another aspect, R² and R³ in structure I are each a methyl group. In another aspect, R² and R³ in structure I are each a branched alkyl group (e.g., 2-ethylhexyl group). In another aspect, R² and R³ in structure I are together part of a silicocycloalkyl group having 4 to 7 atoms. An example of a silicocycloalkyl group is depicted below, where the silicocycloalkyl group has four atoms (one silicon atom and three carbon atoms).

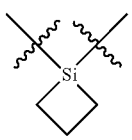

In one aspect, R⁵ and R⁶ in structure I are each a $C_1$ to $C_{10}$ alkyl group. In another aspect, R⁵ and R⁶ in structure I are the same $C_1$ to $C_{10}$ alkyl group. In another aspect, R⁵ and R⁶ in structure I are each a methyl group.

In one aspect, R¹ and R⁴ are independently a heteroaryl group bonded to the phenyl ring via a carbon atom of the heteroaryl group. In this aspect, the heteroaryl group is covalently bonded to each phenyl ring by a carbon atom present in the heteroaryl group. An example, of this is depicted in structure X below, where R¹ and R⁴ in structure I are each a substituted indolizine group. Here, the substituted indolizine group X (i.e., heteroaryl group) is covalently bonded to a carbon atom of the pyrrole ring of the indolizine group

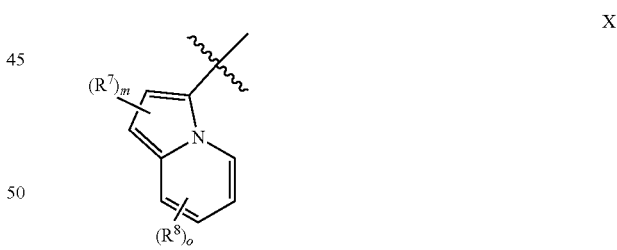

wherein

R⁷ is hydrogen, an alkyl group or an aryl group, where m is 1 or 2, and n is 1 or 2; and R⁸ is hydrogen or an aryl group, where o is 1, 2, or 3, and p is 1, 2, or 3.

In another aspect, R¹ and R⁴ in structure I are the same substituted indolizine group. In another aspect, R¹ and R⁷ in structure I are different substituted indolizine groups.

Figure 1:
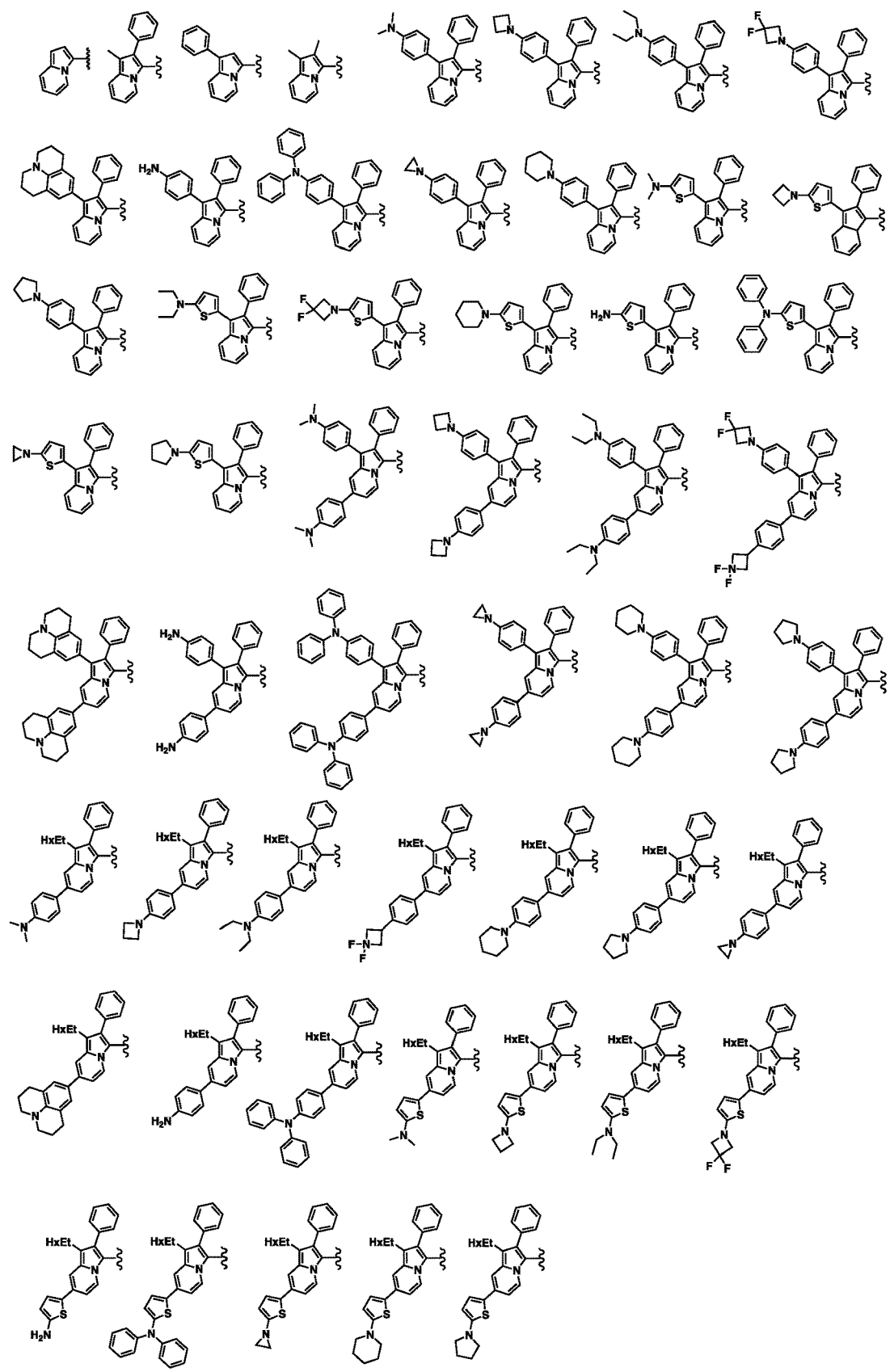
FIGS. 1 and 2 show examples of a substituted indolizine groups that can be present in the silicone-based compounds described herein.
Figure 2:
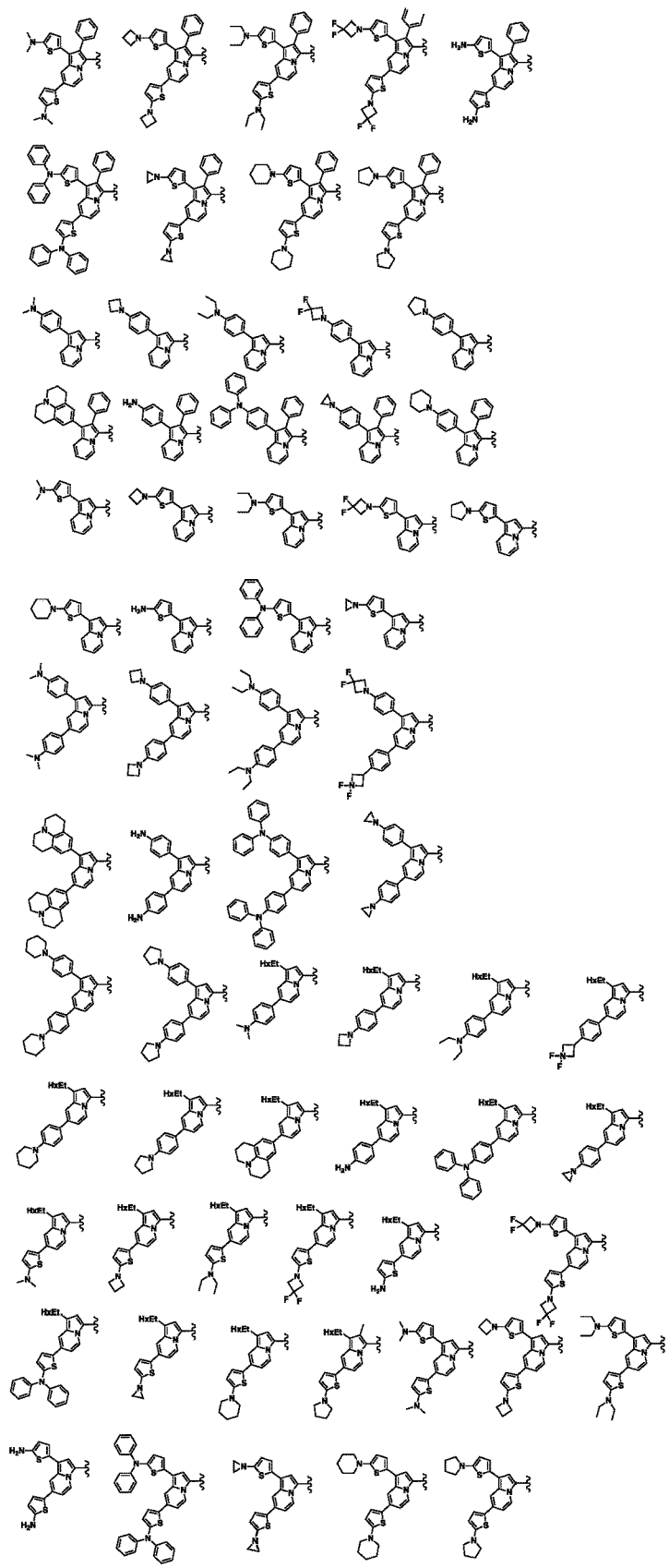

In one aspect, the substituted indolizine group is one of the structures as provided in FIGS. 1 and 2.

In one aspect, the silicone-based compound has the structure II

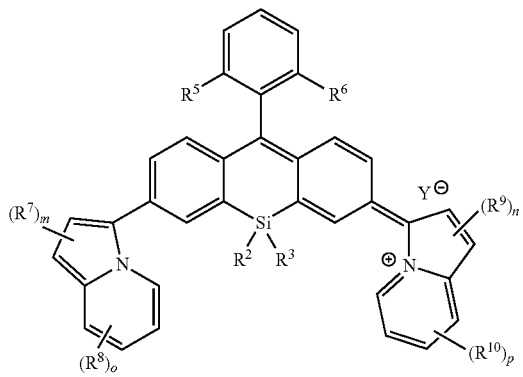

II wherein
R[7] and R[9] are independently hydrogen, an alkyl group or an aryl group, where m is 1 or 2, and n is 1 or 2;
R[8] and R[10] are independently hydrogen or an aryl group, where o is 1, 2, or 3, and p is 1, 2, or 3; and
R[2], R[3], R[5], and R[6] are as defined above.

In one aspect, when m in structure II is 2, each R[7] group can be the same group or different group. In one aspect, when m is 2 in structure II, the first R[7] group is an alkyl group and the second R[7] group is an aryl group. In one aspect, the alkyl group is a $C_1$ to $C_{10}$ alkyl group and the aryl group is a phenyl group.

In another aspect, when n in structure II is 2, each R[9] group can be the same group or different group. In one aspect, when n is 2 in structure II, the first R[9] group is an alkyl group and the second R[9] group is an aryl group. In one aspect, the alkyl group is a $C_1$ to $C_{10}$ alkyl group and the aryl group is a phenyl group.

In another aspect, when o and p in structure II is 2 or 3, each R[8] and R[10] group, respectively, can be the same group or different group. In one aspect, each R[8] and R[10] is an unsubstituted or substituted phenyl group. In another aspect, each R[8] and R[10] is a phenyl group substituted with an amino group.

In another aspect, R[7], R[8], R[9], and R[10] can independently be one of the groups as provided in FIG. 3.

In one aspect, the silicone-based compound has the structure III

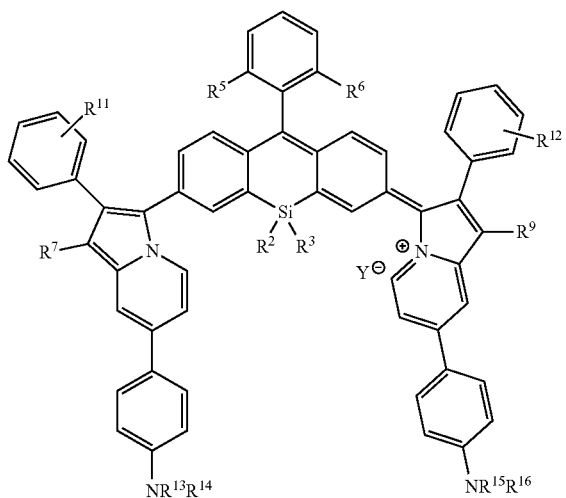

III wherein
R[7] and R[9] are independently an alkyl group or an unsubstituted or substituted phenyl group;
R[11] and R[12] are independently hydrogen, an alkyl group, an alkoxy group, an unsubstituted or substituted phenyl group, an alkenyl group, or an alkynyl group;
R[13], R[14] R[15], and R[16] are independently hydrogen, an aryl group, or an alkyl group; and
R[2], R[3], R[5], and R[6] are as defined above.

In one aspect, R[7] and R[9] in structure III are each a $C_1$ to $C_{10}$ alkyl group. In another aspect, R[13], R[14] R[15], and R[16] in structure III are each an alkyl group. In another aspect, R[2] and R[3] in structure III are each a $C_1$ to $C_{10}$ alkyl group. In another aspect, R[5] and R[6] in structure III are each a $C_1$ to $C_{10}$ alkyl group.

In one aspect, R[11] and R[12] in structure III are each hydrogen. In another aspect, R[11] and R[12] in structure III are each an alkyl group or alkoxy group substituted with an anionic group. In certain aspects, one or more anionic groups can be incorporated into the compounds described herein to increase the water solubility of the compound. In one aspect, R[11] and R[12] in structure III each have the formula —O(CH$_2$)$_q$X or —(CH$_2$)$_q$X, where q is an integer from 1 to 10, and X is the anionic group. In one aspect, the anionic group is a sulfate group, a sulfonate group, a phosphate group, a phosphonate group, or a carboxylate group. Exemplary structures possessing an anionic group are provided in FIG. 4.

In another aspect, R[11] and R[12] in structure III are each an alkyl group or alkoxy group substituted with an alkenyl group or an alkynyl group. In certain aspects, one or more alkenyl or alkynyl groups can be incorporated into the compounds described herein so that the compounds are bioconjugatable. In one aspect, R[11] and R[12] in structure III each have the formula —O(CH$_2$)$_q$Z or —(CH$_2$)$_q$Z, where q is an integer from 1 to 10, and Z is the alkenyl group or alkynyl group. Exemplary structures possessing an alkynyl group are provided in FIG. 5.

In another aspect, the silicone-based compounds have the structure IV

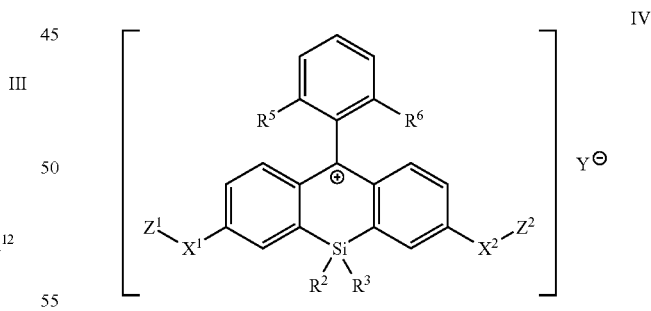

IV wherein
R[2] and R[3] are each an alkyl group or an aryl group;
R[5] and R[6] are independently hydrogen, an alkyl group, or an alkoxy group, wherein
R[5] and R[6] are not both hydrogen;
X[1] and X[2] are independently an alkenyl group or an alkynyl group;
Z[1] and Z[2] are independently an aryl group; and
Y is a counterion.

In one aspect, $X_1$ and/or $X_2$ can be a substituted or unsubstituted diene group or triene group. In another aspect, $X_1$ is an alkene group (—CH=CH—) and $X_2$ is a diene group (—CH=CH—CH=CH—).

In one aspect, the silicone-based compounds have the structure V

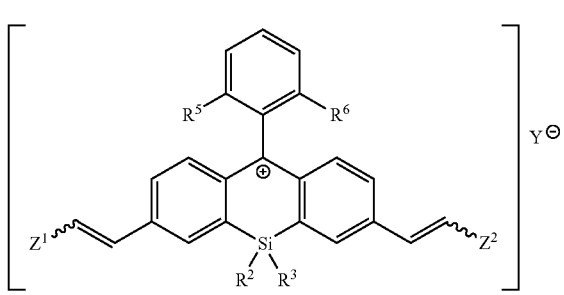

where $R^2$, $R^3$, $R^5$, $R^6$, $Z^1$, and $Z^2$ are each defined with respect to structure IV.

The stereochemistry about each carbon-carbon double bond can be E or Z in structure V. In one aspect, both carbon-carbon double bonds in structure V have Z stereochemistry. In another aspect, both carbon-carbon double bonds in structure V have E stereochemistry. In another aspect, one carbon-carbon double bond in structure V has Z stereochemistry and the other carbon-carbon double bond has E stereochemistry.

In one aspect, $Z^1$ and $Z^2$ in structure V is a polycyclic group with 2 to 6 fused rings. In one aspect, the polycyclic group possesses one or more heteroatoms in the ring system. In another aspect, the polycyclic group includes one or more aromatic rings with one or more heterocyclic rings. In one aspect, the polycyclic group has the structure VI or VII

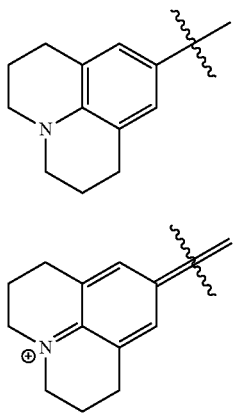

In one aspect, $X^1$—$Z^1$ in structure IV is structure VI and $X^2$—$Z^2$ in structure IV is structure VII In another aspect, $X^1$—$Z^1$ and $X^2$—$Z^2$ in structure IV can be one of the groups as provided in FIGS. 6-8.

The silicone-based compounds described herein are salts, where the compounds are cationic compounds with the counter ion Y. The counterion Y can be any suitable anion such as, for example, a halide, a perchlorate, or carboxylate.

FIG. 9 provides one approach to synthesizing the silicone-based compounds described herein. Referring to FIG. 9, the synthesis begins with the oxidation of compound A to produce compound B. The indolizine heterocycles C are next coupled via CH-activation with compound B yielding the indolizine substituted product D. The final product E is then synthesized by reacting compound D with RLi or RMgBr followed by work up with acid HY to produce the silicone-based compounds E. The Examples provide non-limiting procedures for synthesizing and purifying the silicone-based compounds described herein.

Pharmaceutical Compositions

When used in biological application, the silicone-based compounds described herein can be formulated as pharmaceutical compositions comprising an effective amount of at least one disclosed compound and a pharmaceutically acceptable carrier. As used herein, "pharmaceutically acceptable carrier" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitoneally, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In certain aspects, to increase the water solubility of the silicone-based compounds, the compound can be encapsulated in one or more polymers having hydrophobic and hydrophilic regions. In one aspect, the polymer is an amphiphile possessing hydrophilic and lipophilic groups capable of forming micelles or liposomes. The amphiphiles should be biocompatible such that they possess minimal toxicity. Amphiphiles useful herein for preparing liposomes and micelles include homopolymers, copolymers, block-copolymers produced from biocompatible and biodegradable materials. Examples of such polymers include, but are not limited to, poly(amino acids); polylactides; poly(ethyleneimines); poly(dimethylaminoethylmethacrylates), copolymers of polyethyelene glycol and hydroxyalkyl acrylates and acrylamides (e.g., N-(2-hydroxypropyl) methacrylamide), PEG-poly(α-amino acids), poly(L-lactic acid)-poly (ethylene glycol) block copolymers, or poly(L-histidine)-poly(ethylene glycol) block copolymers.

In one aspect, the polymer is a polyalkylene phospholipid. For example, the polymer can be a phospholipid with polyethylene glycol covalently bonded to the phospholipid. An example of such a polymer is DSPE-mPEG, which is a polyethylene glycol derivative of 1,2-distearoyl-sn-glycero-3-PE. The molecular weight of the polyethylene glycol unit can be from 500 Da to 10,000 Da.

In another aspect, the polymer is a poloxamer. In one aspect, the poloxamer is a nonionic triblock copolymer composed of a central hydrophobic chain of polyoxypropylene (e.g., (poly(propylene oxide)) flanked by two hydrophilic chains of polyoxyethylene (e.g., poly(ethylene oxide)). In one aspect, poloxamer has the formula $$HO(C_2H_4O)_b(C_3H_6O)_a(C_2H_4O)_bOH$$

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the tradename Pluronic® manufactured by BASF. Non-limiting examples of poloxamers useful herein include, but are not limited to, Pluronic® F68, P103, P105, P123, F127, and L121.

The Examples provide non-limiting procedures for encapsulating the silicone-based compounds described herein.

Applications

The silicone-based compounds described herein have an absorption extending into the SWIR region and an emission maximum in the SWIR region, which makes the compounds very useful in numerous applications. Additionally, the silicone-based compounds possess deeper SWIR photon use with increased photostability. Furthermore, by exchanging the oxygen atom of the core indolizine for a silicon atom, exceptionally deep SWIR long wavelength emitters can be produced.

In one aspect, the silicone-based compound has an emission maximum of at least 1,300 nm and an onset of emission greater than 1,500 nm. In another aspect, the compound has an emission maximum of about 1,300 nm to about 1,500 nm, or about 1,300 nm, 1,325 nm, 1,350 nm, 1,375 nm, 1,400 nm, 1,425 nm, 1,450 nm, 1,475 nm, or 1,500 nm, where any value can be a lower and upper endpoint of a range (e.g., 1,325 nm to 1,400 nm).

In another aspect, the silicone-based compounds have a quantum yield greater than 0.03%. In another aspect, the indolizine compounds have a quantum yield greater than 0.03% to about 0.06%, or about 0.035%, 0.04%, 0.045%, 0.05%, 0.055%, or 0.06%, where any value can be a lower and upper endpoint of a range (e.g., 0.04% to 0.055%).

Due to the unique absorption and emission properties of the silicone-based compounds described herein, they are useful in biological imaging. In one aspect, the silicone-based compound can be administered to a subject at a location to be imaged. The administration of the silicone-based compound can be performed using techniques known in the art for formulating and administering imaging agents. After administration, the region to be imaged is illuminated with light at a sufficient wavelength and duration to excite the silicone-based compound to produce an excited compound that will fluoresce. The fluorescence of the excited compound can then be detected using imaging devices known in the art for detecting and quantifying fluorescence.

Due to the fact that the silicone-based compounds described herein have an absorption extending into the SWIR region and an emission maximum in the SWIR region, high resolution during imaging is possible. Another unique feature of the silicone-based compounds described herein is that different silicone-based compounds with different absorption and emission properties can be administered to the subject.

The silicone-based compounds described herein are also useful in non-biological applications. For example, the silicone-based compounds can be incorporated or used in a device such as, for example, a night vision device, a solar cell, or an organic light emitting diode, secure display technologies (NIR/SWIR OLEDs), optical telecommunications, solar cells, and NIR/SWIR photodetectors for instruments and applications such as night vision.

Aspects

The present disclosure can be described in accordance with the following numbered aspects, which should not be confused with the claims.

Aspect 1. A compound having the structure I

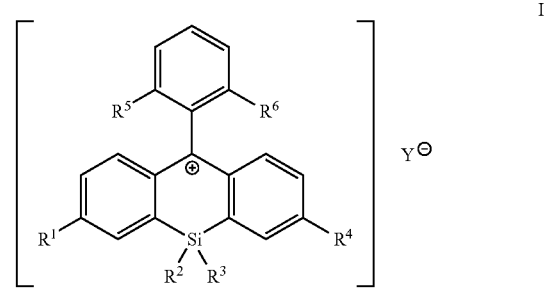

wherein $R^1$ and $R^4$ are independently a heteroaryl group bonded to the phenyl ring via a carbon atom of the heteroaryl group;

$R^2$ and $R^3$ are each an alky group or an aryl group;

$R^5$ and $R^6$ are independently hydrogen, an alkyl group, or an alkoxy group, wherein $R^5$ and $R^6$ are not both hydrogen; and Y is a counterion.

Aspect 2. The compound of Aspect 1, wherein $R^2$ and $R^3$ are each a $C_1$ to $C_{10}$ alkyl group.

Aspect 3. The compound of Aspect 1 or 2, wherein $R^5$ and $R^6$ are each a $C_1$ to $C_{10}$ alkyl group.

Aspect 4. The compound of Aspect 1 or 2, wherein $R^5$ and $R^6$ are each a methyl group.

Aspect 5. The compound in any one of Aspects 1-4, wherein $R^1$ and $R^4$ are each a substituted indolizine group.

Aspect 6. The compound in any one of Aspects 1-5, $R^5$ and $R^6$ are each a methyl group, $R^2$ and $R^3$ are each the same $C_1$ to $C_{10}$ alkyl group, and $R^1$ and $R^4$ are each the same substituted indolizine group.

Aspect 7. The compound of Aspect 1, wherein the compound has the structure II

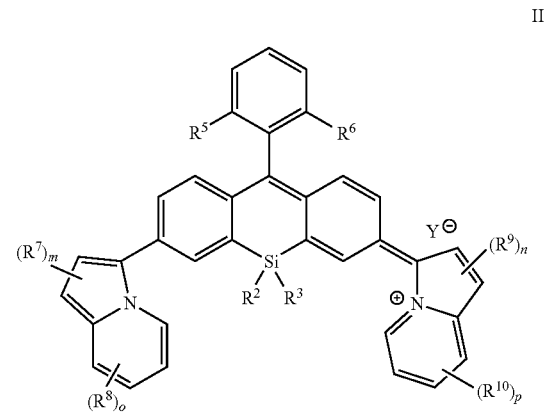

wherein

R[7] and R[9] are independently hydrogen, an alkyl group or an aryl group, where m is 1 or 2, and n is 1 or 2; and R[8] and R[10] are independently hydrogen or an aryl group, where o is 1, 2, or 3, and p is 1, 2, or 3.

Aspect 8. The compound of Aspect 7, wherein m is 2, wherein the first R[7] group is an alkyl group and the second R[7] group is an aryl group.

Aspect 9. The compound of Aspect 7 or 8, wherein n is 2, wherein the first R[9] group is an alkyl group and the second R[9] group is an aryl group.

Aspect 10. The compound of Aspect 8 or 9, wherein the alkyl group is a $C_1$ to $C_{10}$ alkyl group and the aryl group is a phenyl group.

Aspect 11. The compound in any one of Aspects 7-10, wherein o is 1, p is 1, and R[8] and R[10] are each an unsubstituted or substituted phenyl group.

Aspect 12. The compound of Aspect 11, wherein the phenyl group is substituted with an amino group.

Aspect 13. The compound of Aspect 1, wherein the compound has the structure III

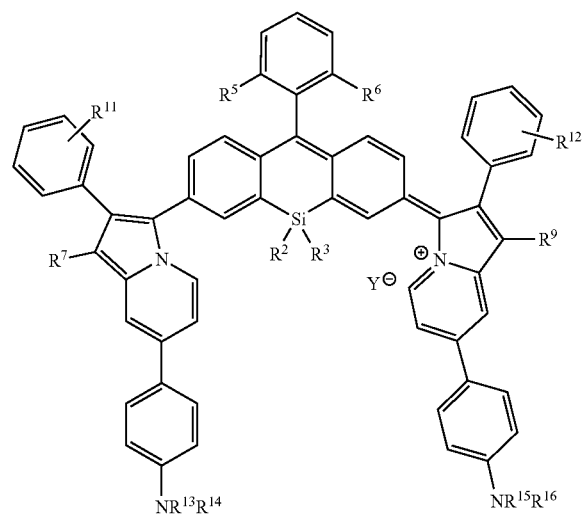

wherein

R[7] and R[9] are independently an alkyl group or an unsubstituted or substituted phenyl group;

R[11] and R[12] are independently hydrogen, an alkyl group, an alkoxy group, an unsubstituted or substituted phenyl group, an alkenyl group, or an alkynyl group; and R[13], R[14] R[15,] and R[16] are independently hydrogen, an aryl group, or an alkyl group.

Aspect 14. The compound of Aspect 13, wherein R[7] and R[9] are each a $C_1$ to $C_{10}$ alkyl group.

Aspect 15. The compound of Aspect 13 or 14, wherein R[11] and R[12] are each hydrogen.

Aspect 16. The compound of Aspect 13 or 14, wherein R[11] and R[12] are each an alkyl group or alkoxy group substituted with an anionic group.

Aspect 17. The compound of Aspect 16, wherein the anionic group is a sulfate group, a sulfonate group, a phosphate group, a phosphonate group, or a carboxylate group.

Aspect 18. The compound of Aspect 13 or 14, wherein R[11] and R[12] are each an alkyl group or alkoxy group substituted with an alkenyl group or an alkynyl group.

Aspect 19. The compound in any one of Aspects 13 to 18, wherein R[13], R[14] R[15], and R[16] are each an alkyl group.

Aspect 20. The compound in any one of Aspects 13 to 19, wherein R[2] and R[3] are each a $C_1$ to $C_{10}$ alkyl group.

Aspect 21. The compound in any one of Aspects 13 to 20, wherein R[5] and R[6] are each a $C_1$ to $C_{10}$ alkyl group.

Aspect 22. The compound of Aspect 1, wherein the compound has the following structure

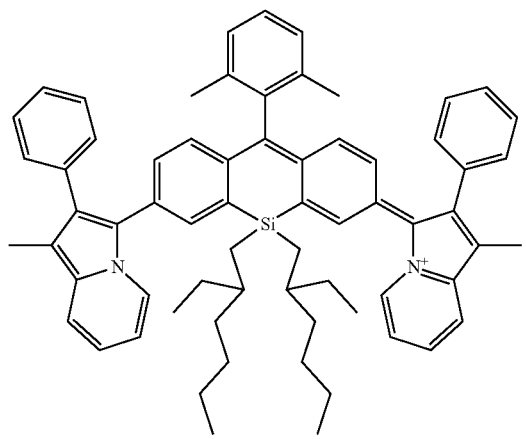

-continued

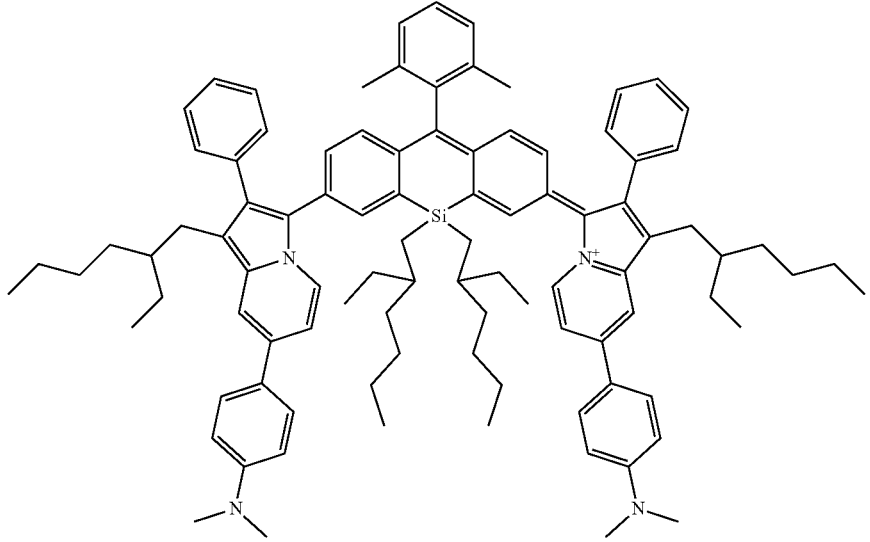

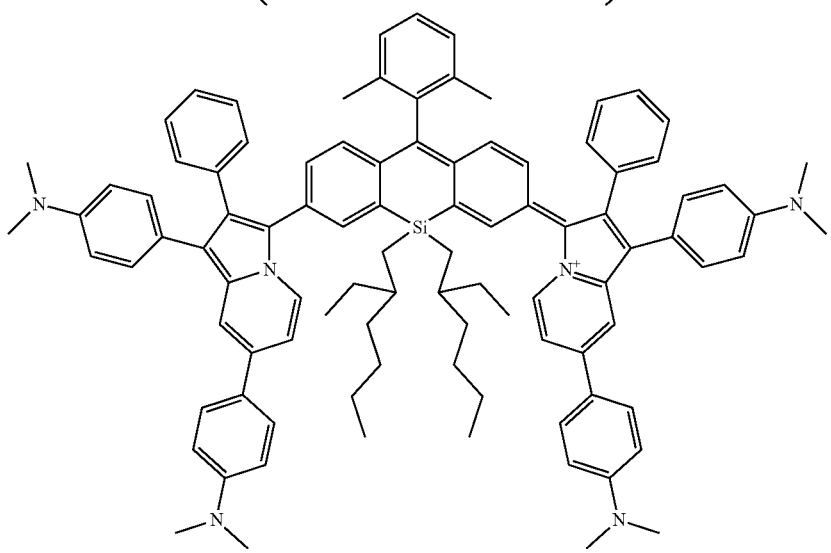

Aspect 23. A compound having the structure IV

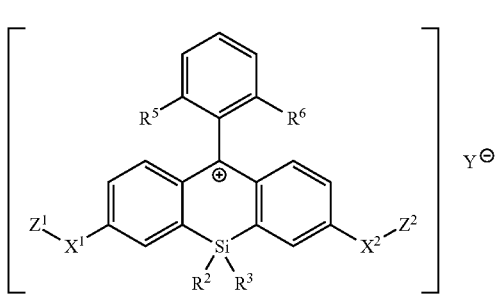

wherein
R² and R³ are each an alkyl group or an aryl group;
R⁵ and R⁶ are independently hydrogen, an alkyl group, or an alkoxy group, wherein R⁵ and R⁶ are not both hydrogen;
X¹ and X² are independently an alkenyl group or an alkynyl group;
Z¹ and Z² are independently an aryl group; and
Y is a counterion.

Aspect 24. The compound of Aspect 23, wherein the compound has the structure V

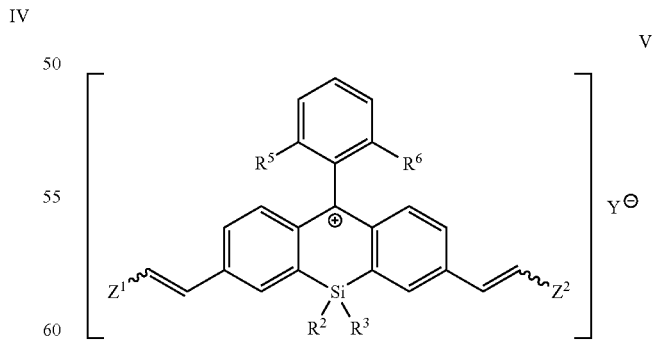

Aspect 25. The compound of Aspect 23 or 24, wherein Z¹ and Z² each have the structure VI or VII

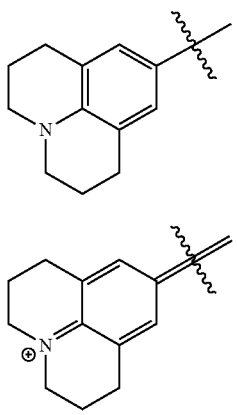

VI

VII

Aspect 26. The compound in any one of Aspects 1-25, wherein $Y^\circ$ is a halide, perchlorate, or carboxylate.

Aspect 27. The compound in any one of Aspects 1-26, wherein the compound has a quantum yield greater than 0.03%.

Aspect 28. The compound in any one of Aspects 1-26, wherein the compound has an emission maximum of at least 1,300 nm and an onset of emission greater than 1,500 nm.

Aspect 29. A composition comprising an encapsulated compound in any one of Aspects 1-28.

Aspect 30. The liposome of Aspect 29, wherein the liposome comprises polyalkylene phospholipid or a poloxamer.

Aspect 31. A pharmaceutical composition comprising the compound in any one of Aspects 1-28 and a pharmaceutically acceptable carrier.

Aspect 32. A device comprising a compound in any one of Aspects 1-28.

Aspect 33. The device of Aspect 32, wherein the device comprises a night vision device, a solar cell, or an organic light emitting diode.

Aspect 34. A method for imaging a tissue in a subject, the method comprising
  (a) administering the compound in any one of Aspects 1-28;
  (b) illuminating the tissue in the subject with light at a sufficient wavelength to excite the compound to produce fluorescence; and
  (c) detecting the fluorescence produced by the excited compound.

Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure.

A target silicon-based dye was synthesized starting from 3,7-dichloro-5,5-dimethyl-5,10-dihydrodibenzo[b,e]siline (FIG. 10). The first reaction was a facile oxidation that yielded the product in 87% yield. The Phlndz heterocycles could be coupled via CH-actiation conditions, yielding the indolizine substituted product in near quantitative yield. The product, $^{Tol}$SiRoslndz, could then be synthesized via a Grignard reaction using o-tolylmagnesiumbromide in THF followed by an acid work up with 2.0 M $HClO_4$ upon completion of the addition of the Grignard substituent. Purification via cyano silica gel yielded the pure dye.

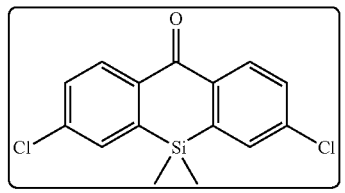 [SMILES: C[Si]1(C)c2cc(Cl)ccc2C(=O)c2ccc(Cl)cc21]

3,7-dichloro-5,5-dimethyldibenzo[b,e]silin-10(5H)-one: To a round bottom flask was added 3,7-dichloro-5,5-dimethyl-5,10-dihydrodibenzo[b,e]siline (50 mg, 0.171 mmol), followed by the addition of acetone (2.0 mL), and $KMnO_4$ (68 mg, 0.430 mmol). The reaction was allowed to stir for a half hour at room temperature while monitoring by TLC for the consumption of the starting material. Once complete, the reaction was extracted with $Et_2O$ and brine 3×, dried over $MgSO_4$, and concentrated. The crude material was purified via silica gel chromatography using DCM:Hx as the eluent (1:2) to yield the pure compound in 87% yield (46 mg, 0.149 mmol) as a white waxy solid. $^1$H NMR (400 MHz, $CDCl_3$) δ 8.36 (d, J=8.6 Hz, 2H), 7.61 (d, J=1.8 Hz, 2H), 7.53 (dd, J=8.6 Hz, 2.1 Hz, 2H), 0.52 (s, 6H).

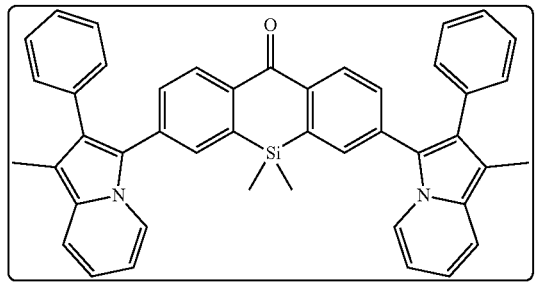

5,5-dimethyl-3,7-bis(1-methyl-2-phenylindolizin-3-yl)-dibenzo[b,e]silin-10(5H)-one: To a flame dried pressure flask under $N_2$ was added 3,7-dichloro-5,5-dimethyldibenzo[b,e]silin-10(5H)-one (0.503 g, 1.637 mmol), Phlndz (0.746 g, 3.60 mmol), $Pd(OAc)_2$ (37 mg, 0.164 mmol) $PCy_3 \cdot HBF_4$ (0.120 g, 0.327 mmol) $Cs_2CO_3$ (3.20 g, 9.82 mmol), and dry toluene (13.1 mL). The flask was sealed and heated at 120° C. for 16 hrs. The reaction was observed to be complete by NMR and was purified straight from the reaction mixture via silica gel column chromatography starting with DCM/Hx (1:1) to remove the excess indolizine and following up with acetone/DCM (1:9) to flush off the product. The pure compound was isolated in near quantitative yield (1.060 g, 1.634 mmol) as an orange solid. $^1$H NMR (400 MHz, $CDCl_3$) δ 8.42 (d, J=8.3 Hz, 2H), 8.25 (d, J=6.9 Hz, 2H), 7.68 (d, J=8.4 Hz, 2H), 7.42 (d, J=9.0 Hz, 2H) 7.31-7.19 (m, 12H), 6.75 (t, J=6.2 Hz, 2H), 6.51 (t, J=6.4 Hz, 2H), 2.35 (s, 6H), 0.02 (s, 6H).

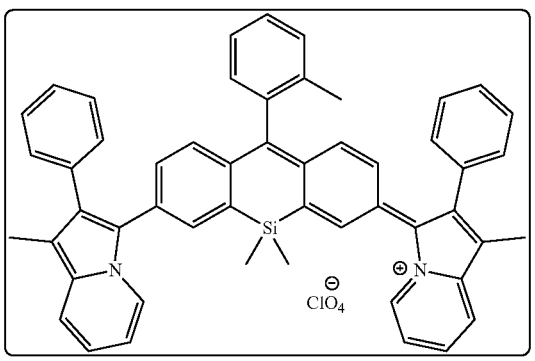

(Z)-3-(5,5-dimethyl-7-(1-methyl-2-phenyl-3H-4I4-indolizin-3-ylidene)-10-(o-tolyl)-5,7-dihydrodibenzo[b,e]silin-3-yl)-1-methyl-2-phenylindolizine. To a flame dried round bottom flask under $N_2$, was added compound 5,5-dimethyl-3,7-bis(1-methyl-2-phenylindolizin-3-yl)dibenzo[b,e]silin-10(5H)-one (50 mg, 0.077 mmol), and dry THF (2.0 mL). While stirring at room temperature, 5 equiv. of o-tolylmagnesium bromide (0.19 mL, 0.385 mmol, 2.0 M in diethyl ether) was added drop wise to the reaction. The reaction was then left to stir at room temperature and monitored via NMR until complete disappearance of the starting material was observed. Once complete, the THF was evaporated under $N_2$ flow and the reaction mixture was diluted using DCM. A few drops of 2.0 M $HClO_4$ was added to the solution, which was transferred into an extraction funnel and shaken well until the formation of a dark blackish-purple color. The DCM layer was then washed with DI water to remove the excess acid and concentrated to ~2 m L, being careful not to dry the solution completely. Diethyl ether was then added to crash out the dye as a dark black solid, which was sonicated, centrifuged, and the supernatant removed with a pipette. The crude product was further purified via cyano-silica chromatography using a 5.5 g RediSep $R_f$ Gold cyano cartridge (20-40 μm, 100 Å) and DCM as an eluent. The product was isolated as a shiny, dark black solid (33%, 21 mg, 0.025 mmol). $^1$H NMR (400 MHz, $CD_2Cl_2$) δ 8.63 (d, J=9.4 Hz, 2H), 7.59 (d, J=11.6 Hz, 2H) 7.53-7.37 (m, 10H), 7.29-7.24 (m, 10H), 7.17 (t, J=10.9 Hz, 2H), 6.93 (t, J=9.3 Hz, 2H), 2.25 (s, 6H), 2.10 (s, 3H), −0.05 (s, 3H), −0.09 (s, 3H).

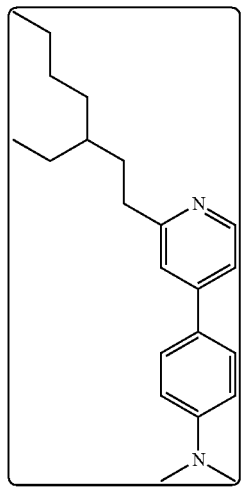 [SMILES: CCCCC(CC)CCc1cc(-c2ccc(N(C)C)cc2)ccn1]

4-(2-(3-ethylheptyl)pyridin-4-yl)-N,N-dimethylaniline. To a flask equipped with a stir bar was added 4-bromo-2-(3-ethylheptyl)pyridine (2.50 g, 8.80 mmol), N,N-dimethyl-4-(4,4,5,5-tetramethyl-1,3,2-dioxaborolan-2-yl)aniline (3.60 g, 12.30 mmol), $K_2CO_3$ (5.1 g, 37.0 mmol), $Pd(PPh_3)_4$ (0.4 g, 0.35 mmol), and 44 mL of 5:3:3 1,4-dioxane:ethanol:$H_2O$ under $N_2$. The reaction mixture was heated to 80° C. for 4 hours while monitoring by TLC plate. The reaction mixture was cooled to room temperature, diluted with $H_2O$ and ethyl acetate. The organic layer was extracted, dried with $Na_2SO_4$, concentrated, and purified by silica gel column chromatography with 10:90 ethyl acetate:hexanes to obtain a yellow oil that gradually solidified (2.68 g, 93%). $^1$H NMR (400 MHz, $CDCl_3$) δ 8.47 (d, J=5.4 Hz, 1H), 7.57 (d, J=8.7 Hz, 2H), 7.32 (s, 1H), 7.27 (d, J=8.24 Hz, 1H), 6.79 (d, J=8.7 Hz, 2H), 3.02 (s, 6H), 2.80 (t, J=6.0 Hz, 2H), 1.72 (m, 2H), 1.30 (m, 9H), 0.88 (m, 6H).

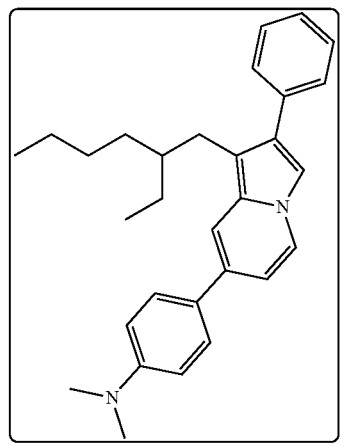 [SMILES: CCCCC(CC)Cc1c(-c2ccccc2)cn2ccc(-c3ccc(N(C)C)cc3)cc12]

4-(1-(2-ethylhexyl)-2-phenylindolizin-7-yl)-N,N-dimethylaniline. To a pressure flask equipped with a stir bar was added acetone (25 mL), 4-(1-(2-ethylhexyl)-2-phenylindolizin-7-yl)-N,N-dimethylaniline (2.00 g, 6.16 mmol), and 2-bromo-1-phenylethan-1-one (1.35 g, 6.77 mmol) under $N_2$. The reaction flask was immersed in a preheated oil bath and heated to reflux for 16 hours. The reaction was cooled to room temperature and the oily precipitate filtered, washed with acetone, then combined with sodium bicarbonate (2.07 g, 24.64 mmol), and 25 mL water. The reaction flask was again heated to reflux for 4 hours, cooled to room temperature, extracted with dichloromethane, dried with sodium sulfate, and evaporated under reduced pressure. It was purified by silica gel chromatography using 100% dichloromethane, 10:90 diethyl ether:dichloromethane to obtain a yellow solid (1.35 g, 68%). $^1$H NMR (400 MHz, $CDCl_3$) δ 7.87 (d, J=9.7 Hz, 1H), 7.50 (m, 5H), 7.40 (t, J=10.1 Hz, 1H), 7.29 (s, 1H), 6.83 (d, J=11.4 Hz, 2H), 6.72 (dd, 1H), 3.00 (s, 3H), 2.82 (m, 2H), 1.44 (m, 1H), 1.16 (m, 8H), 0.76 (m, 6H).

(Z)-3-(10-(2,6-dimethylphenyl)-5,5-bis(2-ethylhexyl)-7-(1-methyl-2-phenylindolizin-3-yl)dibenzo[b,e]silin-3(5H)-ylidene)-1-methyl-2-phenyl-3H-indolizin-4-ium perchlorate (SiRos1): To a flame dried round bottom flask under $N_2$ was added anhydrous THF (1.0 mL) followed by 5,5-bis(2-ethylhexyl)-3,7-bis(1-methyl-2-phenylindolizin-3-yl) dibenzo[b,e]silin-10(5H)-one (30 mg, 0.0355 mmol). 2,6-dimethylphenylmagnesium bromide (0.36 mL, 0.36 mmol) was then added dropwise to the reaction at room temperature, and the reaction subsequently heated to reflux. After an hour, the reaction was quenched with water, extracted over DCM, dried over Na$_2$SO$_4$, and concentrated. DCM (~20 mL) and 2.0 M HClO$_4$ (~20 mL) were then added to the crude mixture and stirred for approximately 6 hours. The solution was observed to change color from a red to a dark black color during this time. The reaction was transferred to a separatory funnel and the DCM layer removed and passed over a dense plug of glass wool in a funnel to remove as much residual water as possible. This mixture was concentrated to ~1 mL and subsequently purified via silica gel chromatography starting with 100% DCM and gradually transitioning to 15% MeCN/DCM to elute the pure dye as a black color (21 mg, 0.0203 mmol, 57%) $^1$H NMR (300 MHz, CD$_2$Cl$_2$) δ 8.65 (d, J=6.9 Hz, 2H), 7.63-7.16 (ms, 23H), 6.95 (m, 2H), 2.22 (s, 6H), 1.98 (s, 6H), 1.15 (m, 2H), 1.03-0.98 (ms, 16H), 0.71 (t, J=6.3 Hz, 6H), 0.65-0.59 (ms, 10H). $^{13}$C NMR (400 MHz, CD$_2$Cl$_2$) δ 140.1, 140.1, 140.0, 139.9, 136.3, 136.2, 134.8, 130.4, 129.4, 129.3, 128.5, 128.2, 126.8, 126.7, 126.6, 126.4, 119.3, 118.7, 118.5, 118.4, 115.7, 115.7, 115.6, 35.6, 35.4, 35.4, 28.8, 28.6, 23.3, 20.1, 14.2, 10.9, 9.5. HRMS m/z calculated for C67H73N$_2$Si [M–ClO$_4^-$]$^+$933.5543, found 933.5586. IR (dispersed in DCM, cm$^{-1}$) 3059, 2955, 2924, 2857, 1619, 1562, 1523, 1473, 1444, 1435, 1346, 1316, 1281, 1204, 1148, 1120, 1092, 1058, 1034.

(Z)-7-(4-(dimethylamino)phenyl)-3-(7-(7-(4-(dimethylamino)phenyl)-1-(2-ethylhexyl)-2-phenylindolizin-3-yl)-10-(2,6-dimethylphenyl)-5,5-bis(2-ethylhexyl)dibenzo[b,e]silin-3(5H)-ylidene)-1-(2-ethylhexyl)-2-phenyl-3H-indolizin-4-ium perchlorate (SiRos2): To a flame dried round bottom flask under N$_2$ was added anhydrous THF (16.0 mL) followed by 3,7-bis(7-(4-(dimethylamino)phenyl)-1-(2-ethylhexyl)-2-phenylindolizin-3-yl)-5,5-bis(2-ethylhexyl)dibenzo[b,e]silin-10(5H)-one (0.804 g, 0.628 mmol). 2,6-dimethylphenylmagnesium bromide (6.3 mL, 6.3 mmol) was then added dropwise to the reaction at room temperature, and the reaction subsequently heated to reflux. After eight hours, the reaction was quenched with water, extracted over Et$_2$O 3×, dried over Na$_2$SO$_4$, and concentrated. DCM (~100 mL) and 2.0 M HClO$_4$ (~100 mL) were then added to the crude mixture and stirred for approximately 6 hours. The solution was observed to change color from a red to a dark brown color during this time. The reaction was transferred to a separatory funnel and the DCM layer removed and passed over a dense plug of glass wool in a funnel to remove as much residual water as possible. The DCM solution was then stirred over Na$_2$CO$_3$ overnight. The next morning the DCM solution was filtered off from the Na$_2$CO$_3$ solids, rinsing thoroughly till the solids were an off white, and the solution condensed to dryness to yield the crude dye. The crude dye was purified via silica gel chromatography starting with 100% DCM and gradually transitioning to 15% MeCN/DCM to elute the pure dye as a brown color (388 mg, 0.264 mmol, 42%) $^1$H NMR (400 MHz, (CD$_3$)$_2$CO) δ 7.78 (br s, 3H), 7.56-7.50 (br ms, 6H), 7.39 (br s, 5H), 6.90 (d, J=8.1 Hz, 4H), 3.09 (s, 12H), 2.78 (s, 6H), 1.49 (m, 2H), 1.26-1.19 (ms, 12H), 1.11 (br s, 13H), 1.04 (br s, 13H), 0.78 (t, J=6.2 Hz, 6H), 0.72-0.66 (ms, 23H). HRMS m/z calculated for C$_{97}$H$_{119}$N$_4$Si [M–ClO$_4^-$]$^+$1368.9238, found 1368.9216. IR (dispersed in DCM, cm$^{-1}$) 3171, 3055, 2951, 2916, 2851, 2801, 1628, 1578, 1561, 1528, 1475, 1436, 1346, 1294, 1263, 1223, 1198, 1182, 1118, 1081, 1037, 1013.

(Z)-3-(7-(1,7-bis(4-(dimethylamino)phenyl)-2-phenylindolizin-3-yl)-10-(2,6-dimethylphenyl)-5,5-bis(2-ethylhexyl)dibenzo[b,e]silin-3(5H)-ylidene)-1,7-bis(4-(dimethylamino)phenyl)-2-phenyl-3H-indolizin-4-ium perchlorate (SiRos3): To a flame dried round bottom flask under N$_2$ was added anhydrous THF (2.0 mL) followed by 3,7-bis(1,7-bis (4-(dimethylamino)phenyl)-2-phenylindolizin-3-yl)-5,5-bis (2-ethylhexyl)dibenzo[b,e]silin-10(5H)-one (100 mg, 0.077 mmol). 2,6-dimethylphenylmagnesium bromide (0.77 mL, 0.77 mmol) was then added dropwise to the reaction at room temperature, and the reaction subsequently heated to reflux. After three hours, the reaction was quenched with water, extracted with DCM 3×, dried over Na$_2$SO$_4$, and concentrated. DCM (~100 mL) and 2.0 M HClO$_4$ (~100 mL) were then added to the crude mixture and stirred for approximately 1 hour. The solution was observed to change color from a red to a dark brown color during this time. The reaction was transferred to a separatory funnel and the DCM layer removed and passed over a dense plug of glass wool in a funnel to remove as much residual water as possible. The DCM solution was then stirred over Na$_2$CO$_3$ for 2 hours. The DCM solution was then filtered off from the Na$_2$CO$_3$ solids, rinsing thoroughly till the solids were off white in color, and the solution condensed to dryness to yield the crude dye. The crude dye was purified via silica gel chromatography starting with 100% DCM and gradually transitioning to 15% MeCN/DCM to elute the pure dye as a black-green color (40 mg, 0.027 mmol, 35%) $^1$H NMR (300 MHz, (CD$_3$)$_2$CO) δ 7.72 (ms, 3H), 7.41 (ms, 8H), 7.33 (m, 4H), 7.20 (d, J=8.3 Hz, 4H), 6.88 (d, J=8.6 Hz, 4H), 6.72 (d, J=8.8 Hz, 4H), 3.07 (s, 12H), 2.97 (s, 12H), 2.77 (s, 6H), 1.29 (m, 2H), 1.13-1.06 (ms, 16H), 0.77-0.66 (ms, 16H). HRMS m/z calculated for C$_{97}$H$_{105}$N$_6$Si [M—ClO$_4^-$]$^+$ 1382.8199, found 1382.8185. IR (dispersed in DCM, cm$^{-1}$) 3174, 3145, 3056, 3026, 2954, 2923, 2856, 2801, 2734, 2642, 2571, 2548, 2463, 2415, 2336, 2217, 2199, 1576, 1560, 1500, 1467, 1437, 1343, 1325, 1291, 1231, 1208, 1186, 1138, 1116, 1054, 1006.

Encapsulation of Silicone-Based Compounds 0.1 mg of silicone-based compound was combined with 10 mg DSPE-mPEG2000 (1% loading of dye by mass) in 3 mL of dichloromethane (DCM) in a 10 mL scintillation vial. The solution was vortexed for 10 seconds to homogenously mix the components. DCM was evaporated from the solution on a rotary evaporator at 50° C. until the solution forms a thin paste around the vial. Subsequently, the vial was placed on high vacuum for a half an hour to remove any residual DCM. Next, 3 mL of D$_2$O was added and the resulting mixture was sonicated for one minute with gentle swirling to dissolve the polymer and dye together. The mixture was syringe filtered (0.45 μm) to remove any unencapsulated compound.

Emission Studies

The emission spectra of the dyes were recorded from 1000-2500 nm using a liquid nitrogen cooled InAs fluorimeter from Horiba. A 980 nm DPSS (diode pumped solid state laser, max power 2 W) laser was used as the excitation source and the chopper signal was split from the chopper control to the lock-in-amplifier as a reference signal and the trigger signal to the laser controller. All studies were performed at 1e-5 M in DCM or 0.1 mg of dye per 3 mL D2O solution (for D2O, the dyes were solubilized in a commercially available DSPE-mPEG2000 nanoparticle, preparation previously supplied).

Stability Study

The introduction of the meta-xylyl ring on the silicon-rosindolizine bridge as found to impart substantial stability compared to a tolyl ring on the silicon-rosindolizine bride. In neutral aqueous solutions, the half-life of the xylyl substituted derivatives SiRos1, SiRos2, and SiRos3, (FIG. 11) was found to be longer than a week while the tolyl derivative has a half life of ~1 hour for some derivatives. This increased stability is critically important to some biological imaging applications. The meta-xylyl substituted derivative retain very similar spectral properties to the tolyl derivatives with absorption and emission observed in the SWIR region. Emissive materials in this spectral region are important to telecommunications and secure displays. Application in night vision, solar cells, and photodetectors are also possible with materials absorbing in this spectral region. These materials are demonstrated emissive in organic solvent (dichloromethane) and in water when encapsulated in a polymer (FIG. 12). The quantum yield is near 0.01-0.05% in these environments with peak emission of SiRos1 at ~1350 nm (FIG. 13) and peak emission of SiRos2>1550 nm.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. A. L. Antaris, H. Chen, K. Cheng, Y. Sun, G. Hong, C. Qu, S. Diao, Z. Deng, X. Hu and B. Zhang, Nature materials, 2016, 15, 235-242.
2. J. Cao, B. Zhu, K. Zheng, S. He, L. Meng, J. Song and H. Yang, Frontiers in bioengineering and biotechnology, 2020, 7, 487
3. F. Ding, Y. Zhan, X. Lu and Y. Sun, Chemical science, 2018, 9, 4370-4380.
4. B. Li, M. Zhao, L. Feng, C. Dou, S. Ding, G. Zhou, L. Lu, H. Zhang, F. Chen and X. Li, Nature communications, 2020, 11, 1-11.
5. L. Lu, B. Li, S. Ding, Y. Fan, S. Wang, C. Sun, M. Zhao, C.-X. Zhao and F. Zhang, Nature communications, 2020, 11, 1-11.
6. Q. Yang, Z. Ma, H. Wang, B. Zhou, S. Zhu, Y. Zhong, J. Wang, H. Wan, A. *Antaris* and R. Ma, Advanced Materials, 2017, 29, 1605497.
7. J. Zhao, D. Zhong and S. Zhou, Journal of Materials Chemistry B, 2018, 6, 349-365.
8. H. Wan, J. Yue, S. Zhu, T. Uno, X. Zhang, Q. Yang, K. Yu, G. Hong, J. Wang and L. Li, Nature communications, 2018, 9, 1-9.
9. W. Xu, D. Wang and B. Z. Tang, Angewandte Chemie, 2020.
10. R. A. Benson, I. B. McInnes, J. M. Brewer and P. Garside, Nature Reviews Rheumatology, 2015, 11, 357.
11. J. A. Cotruvo Jr, A. T. Aron, K. M. Ramos-Torres and C. J. Chang, Chemical Society Reviews, 2015, 44, 4400-4414.
12. X. Qian and Z. Xu, Chemical Society Reviews, 2015, 44, 4487-4493.
13. W. Xu, Z. Zeng, J. H. Jiang, Y. T. Chang and L. Yuan, Angewandte Chemie International Edition, 2016, 55, 13658-13699.
14. L. Li, X. Dong, J. Li and J. Wei, Dyes and Pigments, 2020, 108756.
15. Z. Liu, C. Davis, W. Cai, L. He, X. Chen and H. Dai, Proceedings of the National Academy of Sciences, 2008, 105, 1410-1415.
16. Y. Zhang, Y. Zhang, G. Hong, W. He, K. Zhou, K. Yang, F. Li, G. Chen, Z. Liu and H. Dai, Biomaterials, 2013, 34, 3639-3646.
17. H. S. Choi, W. Liu, P. Misra, E. Tanaka, J. P. Zimmer, B. I. Ipe, M. G. Bawendi and J. V. Frangioni, Nature biotechnology, 2007, 25, 1165-1170.
18. M. Yu, J. Liu, X. Ning and J. Zheng, Angewandte chemie, 2015, 127, 15654-15658.
19. M. Yu, J. Zhou, B. Du, X. Ning, C. Authement, L. Gandee, P. Kapur, J. T. Hsieh and J. Zheng, Angewandte Chemie, 2016, 128, 2837-2841.
20. J. A. Carr, D. Franke, J. R. Caram, C. F. Perkinson, M. Saif, V. Askoxylakis, M. Datta, D. Fukumura, R. K. Jain and M. G. Bawendi, Proceedings of the National Academy of Sciences, 2018, 115, 4465-4470.
21. C. Sun, B. Li, M. Zhao, S. Wang, Z. Lei, L. Lu, H. Zhang, L. Feng, C. Dou and D. Yin, Journal of the American Chemical Society, 2019, 141, 19221-19225.
22. S. Wang, Y. Fan, D. Li, C. Sun, Z. Lei, L. Lu, T. Wang and F. Zhang, Nature communications, 2019, 10, 1-11.
23. S. Zhu, Z. Hu, R. Tian, B. C. Yung, Q. Yang, S. Zhao, D. O. Kiesewetter, G. Niu, H. Sun and A. L. *Antaris*, Advanced Materials, 2018, 30, 1802546.
24. M. Beija, C. A. Afonso and J. M. Martinho, Chemical Society Reviews, 2009, 38, 2410-2433.
25. M. Dai, Y. J. Reo, C. W. Song, Y. J. Yang and K. H. Ahn, Chemical Science, 2020, 11, 8901-8911.
26. N.-Y. Kang, J. Y. Lee, S. H. Lee, I. H. Song, Y. H. Hwang, M. J. Kim, W. H. Phue, B. K. Agrawalla, S. Y. D. Wan and J. Lalic, Journal of the American Chemical Society, 2020, 142, 3430-3439.
27. Y. Koide, Y. Urano, K. Hanaoka, W. Piao, M. Kusakabe, N. Saito, T. Terai, T. Okabe and T. Nagano, Journal of the American Chemical Society, 2012, 134, 5029-5031.
28. A. J. Huckaba, F. Giordano, L. E. McNamara, K. M. Dreux, N. I. Hammer, G. S. Tschumper, S. M. Zakeeruddin, M. Grätzel, M. K. Nazeeruddin and J. H. Delcamp, Advanced Energy Materials, 2015, 5, 1401629.
29. A. J. Huckaba, A. Yella, L. E. McNamara, A. E. Steen, J. S. Murphy, C. A. Carpenter, G. D. Puneky, N. I. Hammer, M. K. Nazeeruddin and M. Grätzel, Chemistry—A European Journal, 2016, 22, 15536-15542.
30. C. S. Rathnamalala, J. N. Gayton, A. L. Dorris, S. A. Autry, W. Meador, N. I. Hammer, J. H. Delcamp and C. N. Scott, The Journal of organic chemistry, 2019, 84, 13186-13193.
31. E. W. Miller, A. E. Albers, A. Pralle, E. Y. Isacoff and C. J. Chang, Journal of the American Chemical Society, 2005, 127, 16652-16659.

What is claimed:
1. A compound having the structure III

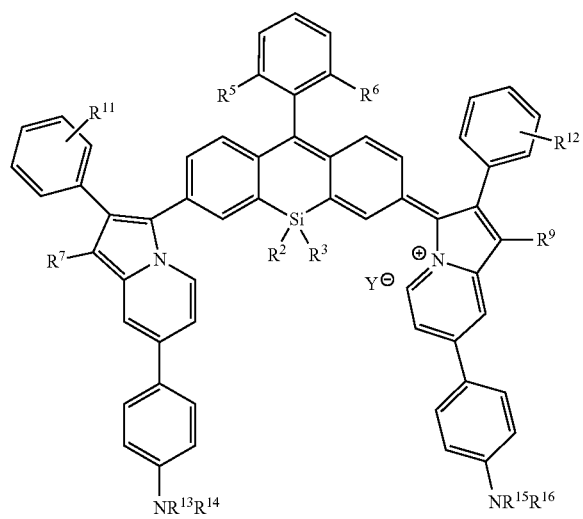

wherein
R$^2$ and R$^3$ are each an alky group or an aryl group;
R$^5$ and R$^6$ are independently hydrogen or an alkyl group, wherein R$^5$ and R$^6$ are not both hydrogen;
R$^7$ and R$^8$ are independently an alkyl group or an unsubstituted or substituted phenyl group;
R$^{11}$ and R$^{12}$ are independently hydrogen, an alkyl group, an alkoxy group, an unsubstituted or substituted phenyl group, an alkenyl group, or an alkynyl group;
R$^{13}$, R$^{14}$ R$^{15}$, and R$^{16}$ are independently hydrogen, an aryl group, or an alkyl group; and
Y is a counterion.

2. The compound of claim 1, wherein R$^7$ and R$^9$ are each a C$_1$ to C$_{10}$ alkyl group.

3. The compound of claim 1, wherein R$^{11}$ and R$^{12}$ are each independently hydrogen, an alkyl group or alkoxy group substituted with an anionic group.

4. The compound of claim 1, wherein R$^{11}$ and R$^{12}$ are each independently an alkyl group or alkoxy group substituted with an alkenyl group or an alkynyl group.

5. The compound of claim 1, wherein R$^{13}$, R$^{14}$ R$^{15}$, and R$^{16}$ are each an alkyl group.

6. The compound of claim 1, wherein R$^2$ and R$^3$, R$^5$, and R$^6$ are each a C$_1$ to C$_{10}$ alkyl group.

* * * * *